(12) United States Patent
Black et al.

(10) Patent No.: US 7,282,613 B2
(45) Date of Patent: Oct. 16, 2007

(54) PROCESS FOR PRODUCING PHENOL AND METHYL ETHYL KETONE

(75) Inventors: Jesse Raymond Black, Katy, TX (US); Jiemin Yang, Houston, TX (US); James Laurel Buechele, Houston, TX (US)

(73) Assignee: Shell Oil Company, Houston, TX (US)

( * ) Notice: Subject to any disclaimer, the term of this patent is extended or adjusted under 35 U.S.C. 154(b) by 554 days.

(21) Appl. No.: 10/761,676

(22) Filed: Jan. 21, 2004

(65) Prior Publication Data

US 2004/0236152 A1 Nov. 25, 2004

Related U.S. Application Data

(60) Provisional application No. 60/447,526, filed on Feb. 14, 2003.

(51) Int. Cl.
*C07C 45/00* (2006.01)
*C07C 39/00* (2006.01)
*C07C 37/68* (2006.01)

(52) U.S. Cl. .................. 568/385; 568/716; 568/754

(58) Field of Classification Search ............... None
See application file for complete search history.

(56) References Cited

U.S. PATENT DOCUMENTS

| | | | |
|---|---|---|---|
| 2,632,026 A | 3/1953 | Conner, Jr. | 260/610 |
| 2,632,773 A | 3/1953 | Armstrong et al. | 260/610 |
| 2,757,209 A | 7/1956 | Joris | 260/621 |
| 3,187,055 A | 6/1965 | Armstrong | 260/610 |
| 3,523,977 A | 8/1970 | Reni et al. | 260/610 |
| 3,907,901 A | 9/1975 | Feder et al. | 260/610 |
| 4,016,213 A | 4/1977 | Yeh et al. | 260/621 |
| 4,358,618 A | 11/1982 | Sifniades et al. | 568/385 |
| 4,431,849 A | 2/1984 | Colvin | 568/799 |
| 5,254,751 A | 10/1993 | Zakoshansky | 568/798 |
| 5,298,667 A | 3/1994 | Iwanaga et al. | 568/385 |
| 5,304,684 A | 4/1994 | Nishida et al. | 568/385 |
| 5,530,166 A | 6/1996 | Zakoshansky et al. | 568/798 |
| 5,767,322 A | 6/1998 | Zakoshansky et al. | 568/571 |
| 5,908,962 A | 6/1999 | Zakoshansky et al. | 568/571 |
| 5,959,155 A | 9/1999 | Ohmae et al. | 568/576 |
| 6,077,977 A | 6/2000 | Gopinathan et al. | 568/571 |
| 6,465,695 B1 | 10/2002 | Fulmer et al. | 568/571 |
| 6,486,365 B1 | 11/2002 | Fulmer et al. | 568/768 |

FOREIGN PATENT DOCUMENTS

| | | |
|---|---|---|
| DE | 1443329 | 1/1970 |
| DE | 2300903 | 8/1973 |
| EP | 0548986 A1 | 6/1993 |
| EP | 0578194 B1 | 1/1994 |
| EP | 0399776 | 9/1994 |
| EP | 1088807 A1 | 4/2001 |
| EP | 1088809 A1 | 4/2001 |
| JP | 62-114922 | 5/1987 |
| JP | 03287574 | 12/1991 |
| JP | 2001097901 | 4/2001 |
| WO | WO 00/14042 | 3/2000 |

OTHER PUBLICATIONS

International Search Report, dated Jul. 14, 2004.

*Primary Examiner*—Paul A. Zucker

(57) ABSTRACT

A process for producing phenol and methyl ethyl ketone (MEK).

191 Claims, 5 Drawing Sheets

PROCESS FOR PRODUCING PHENOL AND METHYL ETHYL KETONE

CROSS-REFERENCE TO RELATED APPLICATIONS

The present application claims the benefit of U.S. Provisional Patent Application Ser. No. 60/447,526, filed Feb. 14, 2003, pending.

FIELD OF THE APPLICATION

The present application relates to a process for producing phenol and methyl ethyl ketone (MEK). The product also may comprise acetone, acetophenone, and combinations of the foregoing.

BACKGROUND

Phenol is an important chemical parent substance with a broad usage spectrum. For example, phenol is used to produce phenol resins, bisphenol A, caprolactam, adipic acid, alkyl phenols, and plasticizers.

In general, phenol is manufactured by oxidizing cumene to form the hydroperoxide of cumene, followed by cleavage of the cumene hydroperoxide with an inorganic acid such as sulfuric acid to form a cumene hydroperoxide cleavage product. The cumene hydroperoxide cleavage product generally contains species such as phenol, acetone, α-methyl styrene (AMS), cumene, cumyl phenol (CP), dimethylbenzyl alcohol (DMBA), acetophenone (AP), AMS dimers (AMSd), tars and heavies, and inorganic acid such as sulfuric acid. Acetone, acetophenone, and phenol are the primary products in this group. Equimolar amounts of acetone and phenol generally are produced by this method.

Although acetone has a variety of uses, acetone generally is not in as high demand as phenol. MEK is a technically important ketone which is used, for example, as a lacquer and as a resin solvent. MEK is a high value ketone which can be produced if s-butylbenzene is used in the production of phenol (rather than cumene). The methods described to date for producing MEK as a co-product in the production of phenol have not proven to be commercially viable.

Commercially viable methods are needed for producing controllable yields of phenol and MEK (and, if desired, acetone) during the manufacture of phenol, particularly methods which are controllable to increase or decrease MEK yield, depending upon market demand.

SUMMARY

Figure 1:
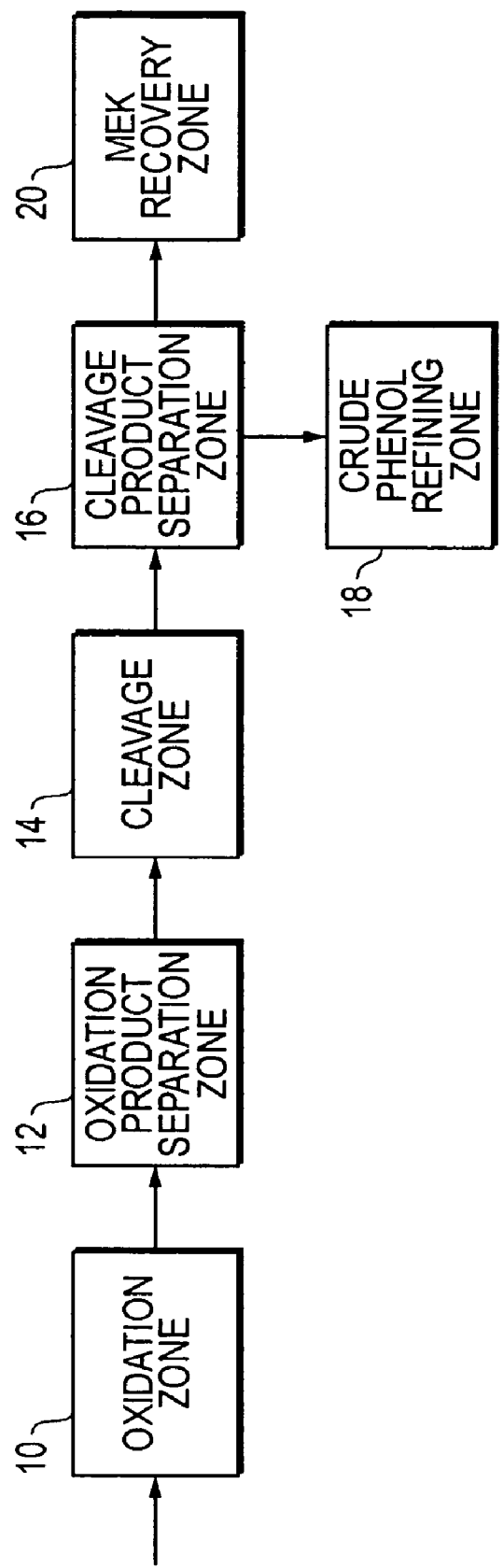
FIG. 1 is a block diagram of the process of the present application.

The application provides a process for producing controllable yields of a combination of products selected from the group consisting of (a) phenol and methyl ethyl ketone (MEK) and (b) phenol, acetone, and MEK. The process comprises:
  feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene;
  exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
  cleaving the product hydroperoxides under cleavage conditions effective to produce a cleavage product comprising a combination selected from the group consisting of (a) phenol and MEK, and (b) phenol, acetone, and MEK; and,
  separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
  recovering one or more products selected from the group consisting of (a) an MEK product and (b) a combination comprising an MEK product and an acetone product.

The application also provides a process for producing controllable yields of phenol, acetone, and methyl ethyl ketone comprising:
  feeding an oxidation feed to an oxidation reactor to produce an oxidation mixture, the oxidation feed comprising a combination comprising cumene and s-butylbenzene, wherein the amount of cumene is from greater than 15 wt. % to less than 30 wt. % relative to the content of s-butylbenzene;
  exposing the oxidation mixture to oxidation conditions effective to produce an oxidation product stream comprising s-butylbenzene hydroperoxide and cumene hydroperoxide; and,
  cleaving the product hydroperoxides under cleavage conditions effective to produce a cleavage product comprising phenol, acetone, methyl ethyl ketone;
  separating the cleavage product under separation conditions effective to separate a crude phenol fraction comprising phenol and a crude ketone stream comprising methyl ethyl ketone (MEK) and acetone; and,
  subjecting the crude ketone stream to ketone separation conditions effective to produce an acetone product and a methyl ethyl ketone product.

The application also provides a process for producing phenol, methyl ethyl ketone, and acetone comprising:
  feeding an oxidation feed comprising a weight ratio of cumene:s-butylbenzene of from about 1:8 (or 12.5 wt.

% cumene) to about 2:1 (or about 66.7 wt. % cumene) to an oxidation reactor to produce an oxidation mixture, exposing the oxidation mixture to oxidation conditions effective to produce an oxidation product stream comprising s-butylbenzene hydroperoxide and cumene hydroperoxide;

cleaving the s-butylbenzene hydroperoxide and cumene hydroperoxide under cleavage conditions effective to produce a cleavage product comprising phenol, acetone, and methyl ethyl ketone;

separating the cleavage product under separation conditions effective to separate a crude phenol fraction comprising phenol and a crude ketone stream comprising methyl ethyl ketone (MEK) and acetone; and, subjecting the crude ketone stream to ketone separation conditions effective to produce an acetone product and a methyl ethyl ketone product.

Description

The present application relates to a process for producing a controllable product slate comprising phenol and methyl ethyl ketone (MEK). The product also may comprise acetone, acetophenone, and combinations thereof at controllable yields.

The term "hydrocarbon" or "hydrocarbons," as used herein, refers to any mixture comprising one or more of cumene, s-butyl benzene, AMS, α-ethyl styrene (AES), 2-phenyl-2-butene (2P2B), and combinations thereof.

Oxidation Zone

Referring to FIG. 1, the process comprises an oxidation zone 10 comprising one or more oxidation reactor(s). The oxidation reactor(s) may be batch reactor(s) or continuous reactor(s). In a preferred embodiment, the oxidation zone 10 comprises a series of continuous reactors.

An oxidation feed is fed to the oxidation reactor(s). The oxidation feed comprises either (a) s-butylbenzene, or (b) a combination comprising an amount of cumene and a content of s-butylbenzene. In the oxidation reactor(s), the oxidation feed is oxidized by molecular oxygen, preferably air, to produce an oxidation product stream. The oxidation product stream is separated in the oxidation reactor(s) into an oxidation bottoms and an oxidation vapor overhead.

Where the oxidation feed is s-butylbenzene, the oxidation product stream comprises s-butylbenzene hydroperoxide, but typically does not comprise a significant amount of cumene hydroperoxide. The operating conditions can be adjusted to coproduce more or less acetophenone (AP).

Where the oxidation feed comprises both cumene and s-butylbenzene, the oxidation product stream comprises s-butylbenzene hydroperoxide and cumene hydroperoxide at high selectivity. The oxidation product stream also comprises certain major byproducts, including but not necessarily limited to acetophenone, di-methyl benzyl carbinol (DMBA), and ethyl methyl benzyl carbinol (EMBA). Finally, the oxidation product stream may comprise minor by-products, including but not necessarily limited to di-cumyl peroxide, di-s-butylperoxide, cumyl s-butyl peroxide, formic acid, acetic acid, methanol, ethanol, methyl hydroperoxide, ethyl hydroperoxide, phenol, acetone, and MEK.

In a preferred embodiment, the oxidation mixture comprises a weight ratio of cumene:s-butylbenzene of from about 1:8 to about 2:1. In percentage terms, the foregoing ratios represent from about 12.5 wt. % cumene to about 66.7 wt. % cumene. In another embodiment, the amount of cumene is from greater than 15 wt. % to less than 30 wt. % relative to the content of s-butylbenzene.

Without limiting the claims to a particular mechanism of action unless expressly stated in a claim, the predominate mechanism for the formation of the major and minor by-products (described previously) is believed to be the free radical decomposition of the s-butyl-benzene hydroperoxide and (if present) the cumene hydroperoxide in the oxidation product.

In the oxidation reactor(s), the oxidation mixture is contacted with an oxygen-containing gas under oxidation conditions comprising an oxidation temperature effective to oxidize s-butylbenzene and (if present) cumene, to produce the respective hydroperoxides. Suitable oxidation temperatures at most oxidation pressures are from about 90° C. to about 150° C. Preferred temperatures will vary depending upon the type of oxidation reactor and the composition of the oxidation feed. Conversion and selectivity to cumene hydroperoxide and s-butylbenzene hydroperoxide increases with an increase in the cumene:s-butylbenzene ratio in the oxidation feed. Conversion also increases with an increase in oxidation temperature.

In a batch oxidation reactor, the oxidation temperature can be adjusted throughout the reaction period to maximize selectivity of the oxidation reaction. Suitable oxidation pressures for batch reactor(s) are from about 0 psig to about 100 psig, preferably from about 15 psig to about 40 psig.

In continuous oxidation reactor(s), the oxidation temperature in each oxidation reactor is selected to maximize selectivity, and will depend upon the composition of the oxidation feed. Suitable oxidation pressures when using continuous reactors generally are from about 0 psig to about 100 psig, preferably from about 15 psig to about 40 psig. Where the oxidation feed comprises a weight ratio of cumene:s-butylbenzene of 2:1. a preferred oxidation temperature for a continuous reactor is from about 100° C. to about 115° C. Where the oxidation feed comprises a weight ratio of cumene:s-butylbenzene of 1:8, a preferred oxidation temperature for a continuous reactor is from about 110° C. to about 130° C.

Oxidation reaction times will vary from about 5 to about 25 hours. The oxidation reaction time in a batch reactor preferably is from about 6 to about 11 hours for all cumene: s-butylbenzene ratios, with the oxidation temperature adjusted to maximize selectivity.

Where the oxidation reactor(s) are continuous oxidation reactors, the "reaction time" typically is referred to as the total residence time. The total residence time is divided between all of the continuous reactors used. For example, if 5 continuous oxidation reactors are operated in series, the residence time for each oxidation reactor is from about 1 to about 5 hours, with oxidation reaction temperatures for each continuous reactor chosen appropriately to achieve desired conversions. The total residence time can be distributed uniformly or non-uniformly between the oxidation reactors.

Both batch reactors and continuous oxidation reactors produce a total conversion of at least about 5% to the desired hydroperoxide, preferably at least s-butylbenzene hydroperoxide, also preferably comprising combined cumene hydroperoxide and s-butylbenzene hydroperoxide. Preferably, total conversion is from about 10% to about 30%, more preferably from about 15% to about 25%.

When carrying out the reaction in multiple continuous reactors, any number of continuous reactors can be employed. Product selectivity is increased by increasing the number of continuous reactors. For example, using two continuous reactors produces a higher yield of the desired hydroperoxides than using only one continuous reactor. In a preferred embodiment, from about 3 to about 8 continuous reactors are used in series. The preferred number of reactors will vary with the cumene:s-butylbenzene ratio of the oxidation feed. For example, where the oxidation feed comprises a ratio of 2:1 cumene:s-butylbenzene, it is preferred to use 4 reactors. In contrast, where the oxidation feed comprises a ratio of 1:8 cumene:s-butylbenzene, it is preferred to use 5 or 6 reactors.

Where the oxidation reactor is one or more continuous reactor(s), the continuous reactor(s) can be a variety of types, including but not necessarily limited to stirred tank reactor(s) or bubble column reactor(s).

When the oxidation reactor(s) are stirred tank reactors(s), oxidation feed addition and oxidation bottoms withdrawal can be from any location. In a preferred embodiment, the oxidation feed is added in the impeller region of a stirred tank reactor(s). In stirred tank reactor(s), it is important to maximize bubble formation and total bubble surface area.

When the oxidation reactor(s) are bubble column reactor(s), the oxidation product is withdrawn from any location in the vessel, but preferably from the bottom of the vessel. Air preferably is added near the bottom of the bubble column reactor through a sparger designed to produce bubbles of small size. The size of the bubbles suitably is about 10 mm or less, preferably 5 mm or less.

Typically, formic acid and acetic acid are produced as oxidation by-products as well as acetophenone (AP), dimethyl benzyl alcohol (DMBA), and ethyl methyl benzyl alcohol (EMBA). Formic and acetic acids catalyze the formation of phenol, which is a poison (or inhibitor) of the main oxidation pathway to make the desired products. Formic and acetic acids, and hence phenol, cause a reduction in the formation of desired products relative to by-products.

Although it is not necessary to use a neutralizing base (or "oxidation base") in the oxidation mixture, the yield of hydroperoxides is increased and attendant by-product formation (e.g., AP, DMBA, EMBA) is decreased by the addition of small amounts of oxidation base. The use of an oxidation base also neutralizes acids, such as acetic and formic acid, as they are formed. In this way, the acids are prevented from forming phenol, and the yield of desired hydroperoxide product is maximized.

Where oxidation base is used, it is preferred to add to the oxidation mixture a solution of oxidation base in an amount sufficient to neutralize the acids formed at the oxidation conditions. If oxidation base is used, it is preferred to add a portion of the oxidation base separately to each oxidation reactor, most preferably to a series of continuous oxidation reactors.

The base solution preferably comprises a concentration of water which is sufficient to act as a carrier for the oxidation base, but insufficient to cause separation of the oxidation mixture into an aqueous phase and an organic phase. The amount of water in the oxidation mixture preferably is from about 400 ppm to about 2 wt. %.

The oxidation base is added in an amount sufficient to produce a molar ratio of base to acids of from about 0:1 to about 6:1, preferably from about 0.5:1 to about 4:1. Suitable oxidation bases are those that have a pH of about 8 to about 12.5 in 1 to 10 wt. % aqueous solution and include, but are not necessarily limited to alkali bases, anhydrous ammonia, and aqueous ammonia. Preferred alkali bases include, but are not necessarily limited to alkali metal carbonates and alkali metal bicarbonates. Suitable alkali metals are potassium and sodium. A preferred alkali base is sodium carbonate.

Ammonia also is a preferred oxidation base. Ammonia can be added as gaseous anhydrous ammonia, as gaseous anhydrous ammonia along with a small water feed, or as aqueous ammonia.

Without limiting the application to a particular mechanism of action, the small amount of water in the oxidation mixture is believed to improve the solubility of the oxidation base in the oxidation mixture, making the oxidation base more readily available to perform the neutralization.

Oxidation is an exothermic reaction, and the heat of reaction is removed from the oxidation reaction mixture during the reaction. For example, some heat is removed by vaporization of hydrocarbon, products and water, if water is present in the oxidation reaction mixture, into the air passing through the reactors, while most heat is removed by heat exchange between the oxidation mixture and cooling fluids. Internal cooling coils can be employed in the oxidation reactors. Preferably, the oxidation reaction mixture is recirculated to heat exchangers external to the oxidation reactor(s).

The oxidation vapor overhead is passed through one or more stages of cooling, during which unreacted hydrocarbons and aqueous material, if present, are condensed and separated from each other. The hydrocarbons are recovered and recycled. The aqueous material typically contains significant amounts of ethanol, methanol, ethyl hydroperoxide, and/or methyl hydroperoxide.

In a preferred embodiment, the oxidation vapor overhead is separated into an oxidation vapor overhead organic fraction ("OVO-OF"), which may be recycled, and an oxidation vapor overhead "aqueous" fraction ("OVO-AF"). The OVO-AF is decomposed under thermal decomposition conditions effective to decompose ethyl hydroperoxide and methyl hydroperoxide, resulting in a thermal decomposition product. The thermal decomposition product comprises alcohols, aldehydes, and/or carboxylic acids. The thermal decomposition conditions comprise a thermal decomposition temperature of from about 80° C. to 250° C., more preferably from 150° C. to 200° C., and a pressure of from about 100 psig to about 200 psig.

In one embodiment, the thermal decomposition conditions comprise adding an inorganic acid to the OVO-AF at a concentration effective to accelerate the decomposition. Suitable inorganic acids include, but are not necessarily limited to sulfuric acid, hydrochloric acid, and phosphoric acid. For purposes of efficiency, a preferred inorganic acid is sulfuric acid, preferably concentrated sulfuric acid. The inorganic acid is added to achieve a concentration of from about 20 ppm to about 100 ppm of the inorganic acid in the OVO-AF. After decomposition is complete, the inorganic acid is neutralized with an alkali base. Preferably, the alkali base has a pH of about 11 or less, even more preferably a pH of from about 10 to about 11. Preferred bases are selected from the group consisting of sodium hydroxide and sodium carbonate.

The thermal decomposition product is subjected to distillation under thermal decomposition product distillation conditions (TDP-distillation conditions) effective to produce a thermal decomposition product organic distillate (TDP-OD) and a thermal decomposition product "aqueous" bottoms (TDP-AB). The TDP-distillation conditions comprise a TDP-distillation temperature effective to remove organic species other than carboxylic acids from the first decomposition product. The TDP-distillation suitably is carried out at atmospheric pressure.

The TDP-OD is disposed of as waste using appropriate means.

Oxidation Product Separation Zone

Referring to FIG. 1, the oxidation bottoms (OB) and an amount of water is fed to an oxidation product separation zone 12. Where no oxidation base is fed to the oxidation, a preferred oxidation product separation zone 12 is one or more strippers. The amount of water fed to the oxidation product separation zone 12 is sufficient to recover methanol, ethanol, methyl hydroperoxide, and ethyl hydroperoxide in the first condenser vapor phase (described below). Generally, an amount of water equivalent to from about 0.1 wt. % to about 1.5 wt. % of the oxidation bottoms is sufficient.

When an oxidation base is fed to oxidation, a preferred oxidation product separation zone 12 is one or more washing decanters used to remove salts formed in the oxidation, followed by one or more strippers. In this embodiment, the oxidation product, water and/or base is fed to the washing decanter(s). Salts in the oxidation product extract into the aqueous layer in the decanter. Some water dissolves in the oxidation product during the wash step. The amount of water dissolved in the oxidation product is sufficient to recover methanol, ethanol, methyl hydroperoxide, and ethyl hydroperoxide in the first condenser vapor phase (described below).

In the one or more strippers, the OB is exposed to stripping conditions effective to concentrate, but ineffective to decompose s-butylbenzene hydroperoxide and (if present) cumene hydroperoxide. The stripping conditions produce a stripper bottoms comprising s-butylbenzene hydroperoxide and (if cumene was fed to oxidation) cumene hydroperoxide and a stripper overhead comprising unreacted hydrocarbon, water, and organic species having a boiling point lower than s-butybenzene hydroperoxide and cumene hydroperoxide. Organic species removed in the stripper overhead include, but are not necessarily limited to the minor by-products delineated above, and small amounts of DMBA, EMBA, and acetophenone. Typically, thermal decomposition of s-butylbenzene hydroperoxide and (if present) cumene hydroperoxide is minimized or avoided at stripper bottoms temperatures of less than 120° C.

Although the use of a single stripper is encompassed by the present invention, a preferred embodiment involves feeding the OB through multiple strippers, more preferably through three strippers in sequence. In a preferred embodiment, the OB is fed through multiple strippers operated at sequentially decreasing pressures to produce a stripper overhead and a stripper bottoms. In this preferred embodiment, the stripping conditions comprise a bottoms temperature of 120° C. or less, preferably less than 120° C., and: a first stripper pressure of from about 40 to about 60 mm Hg; a second stripper pressure of from about 25 to about 35 mm Hg; and, a third stripper pressure of from about 10 to about 20 mm Hg. In a most preferred embodiment: the first stripper conditions comprise a first stripper pressure of about 50 mm Hg; a second stripper pressure of about 30 mm Hg; and, a third stripper pressure of about 15 mm Hg. Greater than about 90 wt. % of the hydrocarbons in the OB are recycled back to the oxidation reactors.

In a preferred embodiment, the first stripper conditions are effective to produce a first stripper overhead comprising a portion of-the cumene (if present) and a portion of the s-butylbenzene in the OB, 99 wt. % or more of the water fed with the OB, 99 wt. % or more of the methanol in the OB, 99 wt. % or more of the ethanol in the OB, 99 wt. % or more of the methyl hydroperoxide in the OB, and 99 wt. % or more of the ethyl hydroperoxide in the OB. In a most preferred embodiment, all of the water, all of the methanol, all of the ethanol, all of the methyl hydroperoxide, and all of the ethyl hydroperoxide in the OB is stripped overhead in the first stripper overhead.

The first stripper preferably comprises at least a first stripper overhead condenser, preferably a multiple first stripper overhead condenser system. The first stripper overhead condenser is operated under partial condensation conditions referred to herein as first stripper overhead condenser conditions. The first stripper overhead condenser conditions comprise a first stripper overhead condensation temperature and a first stripper overhead condensation pressure effective to cause a majority of the cumene (if present) and a majority of the s-butylbenzene in the first stripper overhead to condense, producing a first condenser organic phase. Preferably, the first stripper overhead condenser conditions are effective to condense about 90 wt. % or more of the s-butylbenzene and about 85 wt. % or more of the cumene (if present) in the first stripper overhead into the first stripper overhead first condenser organic phase. The first stripper overhead condenser conditions also comprise a temperature and pressure effective to produce a first condenser vapor phase comprising a majority, preferably about 95 wt. % or more, of the water, the ethanol, the methanol, the methyl hydroperoxide, and the ethyl hydroperoxide in the first stripper overhead.

The first condenser vapor phase is separated from the first condenser organic phase, and the first condenser vapor phase is subjected to second condensation conditions effective to form a second condenser organic phase and a second condenser "aqueous" phase comprising a majority, preferably about 90 wt. % or more, of the ethanol, the methanol, the methyl hydroperoxide, and the ethyl hydroperoxide in the first condenser vapor phase.

The second condenser aqueous phase is separated from the second condenser organic phase, and the second condenser aqueous phase is subjected to thermal decomposition conditions effective to decompose methyl hydroperoxide and ethyl hydroperoxide, producing a thermal decomposition product comprising alcohols, aldehydes, and/or carboxylic acids. The thermal decomposition conditions are the same as described previously for the thermal decomposition of the oxidation vapor overhead aqueous fraction (OVO-AF). The second condenser aqueous phase either is thermally decomposed independently, or the OVO-AF and the second condenser aqueous phase are combined to produce a decomposition mixture which is exposed to the thermal decomposition conditions.

Cleavage Zone

The stripper bottoms comprising one or more of s-butylbenzene hydroperoxide and cumene hydroperoxide is fed to a cleavage zone 14 (FIG. 1). The cleavage zone 14 comprises one or more cleavage reactor(s) in which the stripper bottoms is subjected to a first cleavage reaction and a second cleavage reaction.

Where the oxidation feed comprises s-butylbenzene, the oxidation product generally comprises ethyl methyl benzyl carbinol (EMBA). A cumene oxidation product generally contains dimethylbenzyl alcohol (DMBA). It is desirable during cleavage to maximize conversion of DMBA in the oxidation product to α-methyl styrene (AMS), and to maximize conversion of EMBA in the oxidation product to α-ethyl styrene (AES) and 2-phenyl-2-butene (2P2B) because these compounds can be hydrogenated to produce cumene and s-butylbenzene for recycle back to the oxidation reactors, which increases overall conversion efficiency.

Unfortunately, many cleavage reactions are run at relatively high reaction temperatures. For example, the reaction temperature in typical boiling pot reactions is from about 75° C. to about 85° C. At such high reaction temperatures, significant amounts of DMBA, EMBA, product AMS, product AES, and product 2P2B are converted to "non-recoverable by-products." The present application provides a process for cleaving one or more hydroperoxides selected from the group consisting of s-butylbenzene hydroperoxide, cumene hydroperoxide, and combinations thereof to reduce the production of non-recoverable by-products of DMBA and EMBA.

The cleavage reaction feed to the cleavage zone 14 generally is the stripper bottoms, water, and a ketone stream selected from the group consisting of an acetone stream, an MEK stream, or a mixed acetone/MEK stream. The stripper bottoms comprises hydroperoxides selected from the group consisting of s-butylbenzene hydroperoxide, cumene hydroperoxide, and combinations thereof. It has been found that the feed from the MEK recovery zone is an aid in reducing production of non-recoverable by-products from DMBA and/or EMBA. Water in the amount of 0.5% to 2% of the weight of the remainder of the feed is added to moderate the reaction.

Figure 2:
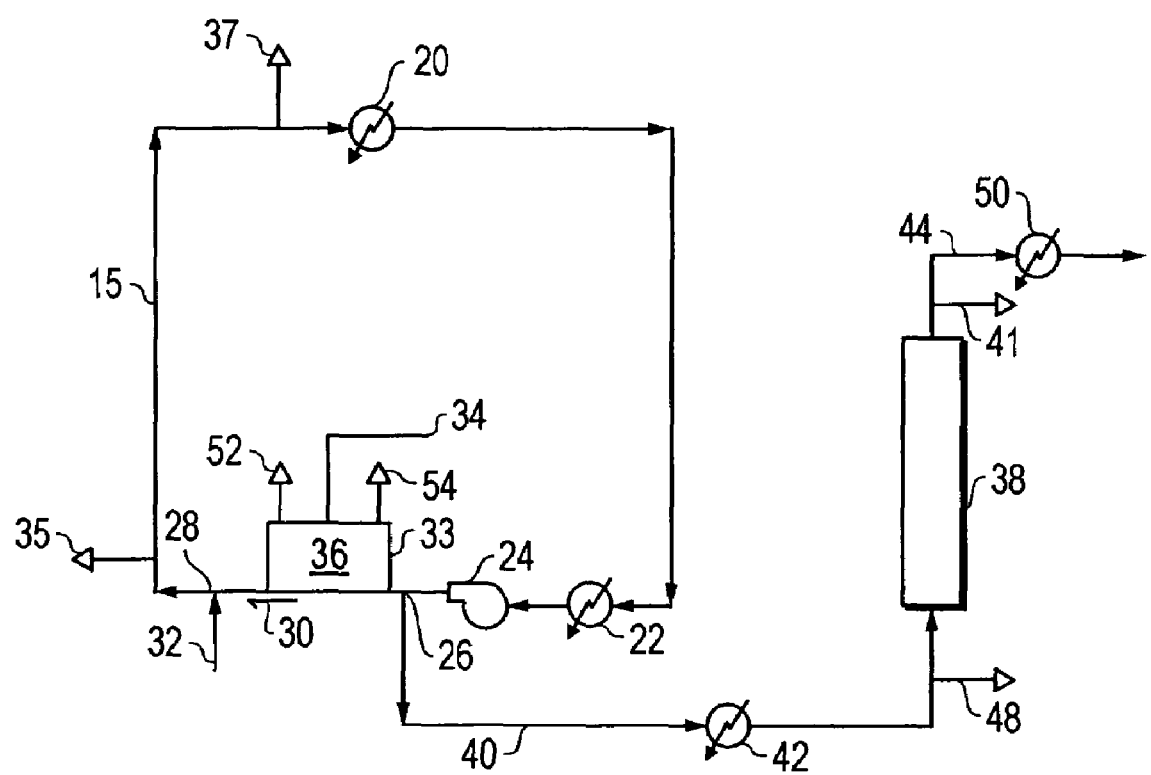
FIG. 2 is a schematic diagram of a preferred cleavage reactor system comprising a pipeline loop reactor and a plug flow reactor.

When the cleavage reaction occurs in a single reactor, the cleavage reaction feed is first exposed to first cleavage reaction conditions (described below) comprising a relatively low temperature, and subsequently exposed to second cleavage-reaction conditions (also described below) in the same reactor. In a preferred embodiment, the stripper bottoms is a first cleavage reactor feed 32 (FIG. 2) to a first cleavage reactor 15.

The cleavage reactor(s) may be a variety of reactor types. Preferred reactors include, but are not necessarily limited to plug-flow reactors ("PFR's"); plug-flow reactors with recycle (PFRR's); and continuous stirred tank reactors (CSTR's).

The first cleavage reactor 15 can be a stirred tank reactor with associated internal or external heat exchange equipment effective to maintain the first cleavage reaction mixture at the first cleavage reaction temperature. In a preferred embodiment the first cleavage reactor 15 is a pipeline loop reactor comprising one or more heat exchangers 20, 22 at appropriate locations to provide cooling sufficient to maintain the first cleavage reaction mixture at the first cleavage reaction temperature. Generally, the first cleavage reaction temperature is from about 45° C. to about 70° C. In a preferred embodiment, the first cleavage reaction temperature is from about 45° C. to about 60° C., more preferably from about 45° C. to about 55° C. The first cleavage reaction pressure is maintained sufficiently high to maintain the first cleavage reaction mixture in the liquid phase. Operating at about 0.5 atmospheres or more generally is sufficient to maintain the first cleavage reaction mixture in the liquid phase.

A pump 24 is installed in the pipeline loop to provide for recirculation of a recycle flow of the first cleavage reaction mixture through the first cleavage reactor 15. A second portion of the first cleavage reaction mixture, the "first cleavage reaction product," is withdrawn from the pipeline loop reactor at a withdrawal point 26 located a short distance upstream of the feed point 28 for the first cleavage reactor feed 32. The recycle flow 30 through the pipeline loop of the first cleavage reactor 15 is much larger than the flow of the first cleavage reactor feed 32 (sometimes referred to as the "first cleavage reactor feed flow 32"). Preferably, the ratio of the recycle flow 30 to the first cleavage reactor feed flow 32 is from about 10:1 to about 100:1 on a weight basis, and more preferably from about 20:1 to about 40:1 on a weight basis.

The first cleavage reaction conditions comprise a first cleavage reaction residence time effective to cleave from about 95% to about 98% of hydroperoxides selected from the group consisting of s-butylbenzene hydroperoxide, cumene hydroperoxide, and combinations thereof. Depending upon the hydroperoxides present in the first cleavage reaction mixture, the hydroperoxides are converted to phenol and a compound selected from the group consisting of methyl ethyl ketone (MEK), acetone, and combinations thereof. Generally, the first cleavage reaction residence time is from about 1 minute to about 10 minutes.

The first cleavage reaction conditions comprise an acid catalyst effective to catalyze the cleavage of s-butylbenzene hydroperoxide and (if present) cumene hydroperoxide. Suitable acid catalysts include, but are not necessarily limited to sulfuric acid, sulfuric acid anhydride, perchloric acid, and phosphoric acid. A preferred acid catalyst is sulfuric acid. In a preferred embodiment, the acid catalyst (preferably concentrated sulfuric acid), is added to a reaction mixture side stream 33 at one or more acid addition points 34. The reaction mixture side stream 33 is located between the first cleavage reaction product withdrawal point 26 and the first cleavage reactor feed point 32.

The acid catalyst is used in an amount of from about 0.005% to about 0.1% by weight based on the first cleavage reactor feed flow 32. Concentrated sulfuric acid and other suitable acid catalysts are commercially available from a variety of sources.

The first cleavage reaction product 40 is fed to a second cleavage reactor 38, preferably a once through plug flow reactor, to produce a second cleavage reaction mixture. The second cleavage reactor 38 is operated at second cleavage reaction conditions effective to produce a second cleavage reaction product 44. The first cleavage reaction product 44 preferably is heated to a second cleavage reaction temperature and maintained in the second cleavage reactor 38 for a second cleavage reaction residence time effective to perform one or more, preferably all of the following functions: cleave 95 wt. % or more of remaining hydroperoxides present in the first cleavage reaction product; convert 70 wt. % or more, preferably 75 wt. % or more, more preferably 85 wt. % or more of DMBA (if present) in the first cleavage reaction product to AMS; and, convert 70 wt. % or more, preferably 75 wt. % or more, more preferably 85 wt. % or more of EMBA (if present) in the first-cleavage reaction product to AES and 2P2B. In this preferred embodiment, selectivity of conversion of DMBA to AMS and/or of EMBA to AES and 2P2B is maximized. Generally the second cleavage reaction residence time is from about 5 seconds to about 1 minute.

Suitably, the second cleavage reaction conditions comprise a second cleavage reaction temperature of from about 60° C. to about 130° C., preferably from about 70° C. to about 120° C. The second cleavage reaction conditions also comprise a second cleavage reaction pressure which, when combined with the second cleavage reaction temperature, is sufficient to maintain the second cleavage reaction mixture in the liquid phase. At the foregoing temperatures, a pressure of about 30 psig or more is sufficient. The second cleavage reaction product 44 is withdrawn from the second cleavage reactor 38 and passed to additional stages for recovering the cleavage products.

Cleaving initially at low temperature increases the yield of AMS, AES, and 2P2B, and reduces the amount of s-butylbenzene and/or cumene required to co-produce a given amount of phenol and MEK and/or acetone. Conversion efficiency is improved and the formation of non-recoverable by-products during cleavage is reduced.

Depending on the ratio of s-butylbenzene hydroperoxide to cumene hydroperoxide, the cleavage produces a second cleavage reaction product 44 with molar acetone:phenol ratios from about 0.8:1 to about 0.23:1 Molar MEK:phenol ratios in the second cleavage reaction product 44 are from about 0.2:1 to about 0.77:1. In a most preferred embodiment, the acetone to phenol ratio in the second cleavage reaction product 44 varies from about 0.44:1 to about 0.25:1.

Reactions which occur at lower temperatures occur in the early cleavage stages, preferably in the first cleavage reaction, which occurs in the first cleavage reactor 15. About 95% to about 98% conversion of hydroperoxides to phenol and MEK and/or acetone is achieved in the first cleavage reactor 15. Reactions which require higher temperatures occur in the later cleavage stages, preferably in the second cleavage reactor 38. The conversion of DMBA to AMS and EMBA to AES and 2P2B require relatively high temperatures of from about 70° C. to about 130° C. and these reactions are postponed, preferably until the first cleavage reaction product 40 reaches the second cleavage reactor 38. At this point, little hydroperoxide remains to be cleaved. The second cleavage reaction conditions can be optimized to maximize the conversion of DMBA to AMS and EMBA to AES and 2P2B.

In a preferred embodiment, the safety of the cleavage reaction is enhanced compared to other embodiments. By using a pipeline loop reactor as the first cleavage reactor 15, it is possible to make multiple exotherm measurements to verify that the reaction is being carried out properly and to control the amount of acid catalyst added to the first cleavage reaction mixture side stream 33. In typical boiling pot cleavage reactors, acid addition-typically is controlled by the single exotherm measurement taken at the sulfuric acid addition point. The single exotherm measurement is made by pumping a small amount of the cleavage reactor mixture out of the reactor at the acid addition point and mixing that small amount of the cleavage reaction mixture with acid. The exotherm generated upon acid addition is measured for process control and to determine if a shutdown is required for safety purposes. If the reaction is running well, then the exotherm measured is moderate (typically 15° C.). If the reaction is running too fast, then no exotherm is measured. If the exotherm is large (about 25° C. or more), then the reaction is running too slowly. The risk of the reaction running too slowly is that a runaway reaction can occur when additional acid is added.

Plug flow reactors (PFR's) and plug flow reactors with recycle (PFRR's) are especially adaptable to multiple exotherm measurements. Controlling acid addition based on multiple exotherm measurements lowers the risk of adding too little or too much acid catalyst to the first cleavage reactor 15 due to an incorrect exotherm measurement by any one failed control system component, and essentially decouples safety components from control components.

In a preferred embodiment, the exotherm preferably is measured across multiple locations. The exotherm is measured across one or more reaction mixture exotherm measurement points, preferably by measuring the temperature increase from measurement point 52 to measurement point 54 along the reaction mixture side stream 33. The exotherm also preferably is measured in the first cleavage reactor 15 across one or more first cleavage reactor (FCR) exotherm measurement points, preferably by measuring the temperature increase from measurement point 35 to measurement point 37 along the first cleavage reactor 15. The exotherm also preferably is measured across the second cleavage reactor, preferably by measuring the temperature rise from measurement point 48 to measurement point 41. The exotherm may be measured using any suitable apparatus, such as thermocouples.

The second cleavage reaction product 44 is cooled, preferably via a heat exchanger 50, and fed to a neutralization apparatus (not shown) where the second cleavage reaction product 44 is subjected to neutralization conditions comprising a neutralizing base effective to produce a neutralized second cleavage reaction product. The neutralization conditions comprise a temperature of from about 40° C. to about 60° C., preferably from about 45° C. to about 50° C., and a pressure sufficient to maintain the second cleavage reaction product in the liquid phase. Atmospheric pressure or higher is sufficient for this purpose. The neutralization apparatus ensures thorough contact of the second cleavage reaction product with the base. Suitable neutralization apparatuses include, but are not necessarily limited to a vessel equipped with a stirrer and a pipe mixer.

Any suitable neutralizing base may be used. Preferred neutralizing bases are alkali bases. Suitable alkali bases include, but are not necessarily limited to hydroxides, carbonates, bicarbonates, and phenates of sodium, potassium, and lithium, and combinations thereof. The alkali base is used in an amount sufficient to maintain the neutralized aqueous fraction (described in the next paragraph) at a pH of from about 5 to about 11, preferably at a pH of from about 5 to about 5.5.

The neutralized second cleavage reaction product is separated into a neutralized organic fraction and a neutralized "aqueous" fraction. The weight ratio of the neutralized organic fraction to the neutralized "aqueous" fraction suitably is from about 1:3 to about 3:1.

At least part of the neutralized "aqueous" fraction preferably is recirculated back to the neutralization apparatus. The remainder of the neutralized "aqueous" fraction may be discarded or recycled to some other part of the process. The salt concentration in the neutralized "aqueous" fraction increases over time, but preferably is maintained at from about 1 to about 30% by weight.

Cleavage Product Separation Zone

In a preferred embodiment, the cleavage product separation zone comprises a Crude Ketone Column (CKC). The neutralized organic fraction, or "CKC feed," is fed to the CKC 16 (FIG. 1) and exposed to CKC conditions effective to produce a bottom crude phenol fraction and a CKC vapor distillate.

The CKC conditions are effective to produce a CKC vapor distillate comprising most of the water (if present), cumene, s-butyl benzene, and AMS in the neutralized organic fraction. The CKC conditions preferably are effective to produce a CKC vapor distillate comprising 99 wt. % or more, preferably all of any water present in the neutralized organic fraction. The CKC conditions also preferably are effective to produce a CKC vapor distillate comprising 75% or more, preferably more than 75% of the hydroxy-ketones in the neutralized organic fraction. The CKC conditions also are effective to produce a crude phenol fraction comprising from about 2 wt. % to about 5 wt. % of a combination of cumene, s-butylbenzene, AMS, AES, and 2P2B.

In a preferred embodiment, the CKC conditions comprise a CKC top temperature of from about 190° C. to about 220° C., preferably from about 203° C. to 207° C., and a CKC top pressure of from about 0 psig to about 10 psig, preferably from about 3 psig to about 7 psig.

The crude phenol fraction is purified to a phenol product in a crude phenol refining zone 18 using known procedures.

The CKC vapor distillate is fed to a CKC vapor condenser and subjected to CKC vapor condenser conditions effective to produce a CKC vapor condensate. The CKC vapor condensate is separated into a CKC vapor condensate organic layer and a CKC vapor condensate aqueous layer. A portion of the CKC vapor condensate aqueous layer—called the "CKC recycle portion"—is fed to the CKC column at a recycle point. Although it is possible for the recycle point to be at a variety of locations on the CKC column, the recycle point most preferably is the same tray at which the neutralized organic fraction is fed to the CKC column. The CKC recycle portion comprises from about 50 wt. % to 95 wt. %, preferably about 75 wt. % to about 80 wt. % of the CKC vapor aqueous layer. The remainder of the CKC vapor condensate aqueous layer and the CKC vapor condensate organic layer are mixed to form a CKC vapor condensate mixture comprising 2 wt. % phenol or less, preferably 1 wt. % phenol or less. The CKC minimum mass reflux ratio to effect this degree of phenol separation is about 0.05/1. In a preferred embodiment, the CKC conditions comprise a mass reflux ratio of from about 0.1/1 to about 0.2/1.

MEK Recovery Zone

MEK product and (if present) acetone are recovered in the MEK recovery zone 20 (FIG. 1).

Where Cumene is not Fed to the Reaction Mixture

Where cumene is not fed to the oxidation reaction, the CKC vapor condensation mixture does not comprise a significant acetone component and is treated to recover MEK product. In this case, the CKC vapor condensate mixture is mixed with an aqueous base, preferably an alkali base, more preferably a sodium containing base, in an amount and concentration effective to catalyze the condensation of aldehydes in the CKC vapor condensate mixture with MEK. The base is fed in sufficient quantity to react with phenol in the CKC vapor condensate mixture to form a phenate, preferably sodium phenate. The resulting mixture, herein called an "MEK recovery mixture" is subjected to MEK separation conditions effective to separate a MEK product.

The MEK separation conditions preferably comprise cooling the MEK recovery mixture to a temperature of from about 35° C. to about 55° C., preferably from about 40° C. to about 45° C., to produce a cooled MEK recovery mixture. The cooled MEK recovery mixture is fed to a MEK recovery mixture decanter where the cooled MEK recovery mixture is separated into a MEK decanter aqueous stream and a MEK decanter organic stream. The MEK decanter aqueous stream preferably is recycled to the cleavage neutralization apparatus. The MEK decanter organic stream comprises MEK, hydrocarbon, other organic species, and any dissolved water. The MEK decanter organic stream is subjected to a minimum of two aqueous washes. The first wash comprises washing the MEK decanter organic stream with aqueous alkali base to remove trace phenol, producing a first washed MEK decanter organic stream.

The first washed MEK decanter organic stream is exposed to first washed MEK decanter organic stream separation conditions effective to produce a first washed MEK decanter aqueous phase and a first washed MEK decanter organic phase. The first washed MEK decanter organic phase is subjected to a second wash with water to remove trace alkali base, producing a twice washed MEK decanter organic stream. The twice washed MEK decanter organic stream is again separated into a final MEK decanter aqueous phase and a MDC feed comprising a final MEK decanter organic phase.

The MDC-feed is fed to a distillation column, called a MEK Dehydration Column (or, a "MDC"). The MDC feed comprises MEK, hydrocarbon, water, and other organic species. The MDC feed is subjected to MDC conditions effective to produce a MDC overhead comprising water and organic species having a boiling point sufficiently lower than MEK to be separated from the MEK, and a MDC bottoms comprising MEK. Organic species having a boiling point sufficiently lower than MEK include, but are not necessarily limited to methanol and ethanol.

In a preferred embodiment, the MDC conditions comprise feeding an entrainer to the MDC to remove the water from the MDC feed with minimal loss of MEK in the MDC overhead. In a preferred embodiment, the entrainer is selected from the group consisting of hexane, cyclohexane, heptane, and combinations thereof. A most preferred entrainer is cyclohexane.

In addition to MEK, the MDC bottoms generally comprises hydrocarbon and other organic species having a boiling point which is the same as or greater than MEK. The boiling point of MEK is 79.6° C.

The MDC conditions comprise a temperature and a pressure which vary relative to one another. For example, when the MDC pressure is from about 3 to about 10 psig, the MDC temperature is from about 75° C. to about 90° C. In a preferred embodiment, the MDC pressure is from about 6 to about 7 psig and the MDC temperature is from about 80° C. to about 85° C.

The MDC conditions also comprise a MDC minimum molar reflux ratio, based on the reflux flow to the overhead water flow, of 5/1. In a preferred embodiment, the MDC molar reflux ratio is about 10/1 to about 20/1.

The MDC bottoms is fed to a MEK product column ("MPC") and subjected to MPC conditions effective to separate the MDC bottoms into a MPC bottoms and a MPC overhead comprising product MEK. In one embodiment, the MPC overhead is the product MEK. In a preferred embodiment, the MPC overhead comprises a MPC purge stream comprising some MEK. In this embodiment, the MPC purge stream is effective to purge organic species having a boiling point less than MEK from the MPC. In this embodiment, a substantially pure MEK product is withdrawn as a side draw. Where purging occurs, the MPC purge stream is recycled back to the first cleavage reactor to provide the benefits to cleavage previously described.

The MPC conditions comprise a temperature and a pressure which vary relative to one another. For example, when the MPC pressure is about 0 psig to about 10 psig, the MPC top temperature is from about 85° C. to about 101° C. Preferably, when the MPC pressure is from about 4 psig to about 6 psig, the MPC top temperature is from about 92° C. to about 95° C. The MPC conditions further comprise a MPC molar reflux ratio, based on reflux flow to product flow, of 0.15 or more, preferably more than 0.15. In a preferred embodiment, the MPC molar reflux ratio is about 1.

The MPC bottoms comprises hydrocarbons and other organic species having a boiling point higher than MEK. The MPC bottoms is subjected to standard post-treatment for analogous streams in a phenol/acetone process before being returned to the oxidation reactor(s).

Where Cumene is Fed to the Oxidation Reaction

Where cumene is fed to the oxidation reaction, a crude acetone/MEK fraction is exposed to acetone/MEK separation conditions in the MEK recovery zone 20 (FIG. 1). In a preferred embodiment, the MEK recovery zone comprises an Acetone Product Column (APC), and the APC feed is the CKC vapor condensation mixture.

The APC feed generally comprises from about 14 wt. % to about 45 wt. % acetone, from about 46 wt. % to about 15 wt. % MEK, about 14 wt. % water (if present), and about 23 wt. % hydrocarbon, together with a variety of by products. In one embodiment, where the oxidation mixture comprises from about 15 wt. % cumene to about 30 wt. % cumene, the APC feed has the following composition:

| APC Feed Composition Range (± indicates small variations about these means are possible) | | |
|---|---|---|
| | Wt % | Wt % |
| Cumene in Oxidation Feed | 15 | 30 |
| Acetone | 16± | 28± |
| MEK | 44± | 32± |
| Water | 14± | 14± |
| Hydrocarbon (mostly s-butyl benzene) | 23± | 23± |
| Phenol | <2% | <2% |
| Other(Aldehydes, Hydroxy-ketones, MO, methanol, ethanol) | <0.5% | <0.5% |

Product acetone is recovered from the APC column either as an APC overhead, or as an APC side draw. When product acetone is recovered as the APC overhead, the product acetone may be tainted with "light" organic species having a boiling point less than acetone. In a preferred embodiment, the APC overhead comprises a purge stream comprising some acetone. In this embodiment, the APC overhead purges the light organic species having a boiling point less than acetone in an APC overhead, and a substantially pure acetone product is withdrawn from the APC column as a side draw. In this embodiment, the APC overhead is sometimes referred to as an "APC purge stream" for convenience. The APC purge stream preferably is recycled to the first cleavage reactor to provide the benefits to cleavage previously described.

The APC conditions preferably comprise feeding an APC base to the APC column. The APC base preferably is an alkali base, most preferably an aqueous solution of alkali base, most preferably an aqueous solution of sodium hydroxide. The APC base is effective to catalyze the condensation of aldehydes in the APC feed with MEK and acetone to produce condensation products. The APC bottoms comprises the condensation reaction products. The APC base also is effective to react with phenol in the APC bottoms to form sodium phenate. Hence, in a preferred embodiment, the APC conditions are effective to produce an APC bottoms comprising MEK, water, hydrocarbon, condensation reaction products, and sodium phenate, and combinations thereof.

The APC conditions comprise an APC pressure of from about 400 to about 500 mm Hg and an APC temperature of from about 30° C. to about 50° C., preferably an APC pressure of about 450 mm Hg and an APC temperature of about 40° C. The APC conditions also preferably comprise an APC minimum molar reflux ratio of about 12, calculated as rate of reflux flow to side draw product flow on a molar basis. In a preferred embodiment, the APC conditions comprise a molar reflux ratio of about 15 or greater.

The APC bottoms is subjected to MEK separation conditions effective to separate a MEK product. The MEK separation conditions preferably comprise cooling the APC bottoms to a temperature of from about 35° C. to about 55° C., preferably from about 40° C. to about 45° C. to produce a cooled APC bottoms. The cooled APC bottoms is fed to an APC bottoms decanter where the cooled APC bottoms is separated into an APC decanter aqueous stream and an APC decanter organic stream. The APC decanter aqueous stream preferably is recycled to the cleavage neutralization apparatus. Like the MEK decanter organic stream, the APC decanter organic stream comprises MEK, hydrocarbon, other organic species, and any dissolved water. Also, like the MEK decanter organic stream, the APC decanter organic stream is subjected to a minimum of two aqueous washes. The first wash comprises washing the APC decanter organic stream with aqueous alkali base to remove trace phenol, producing a first washed APC decanter organic stream.

The first washed APC decanter organic stream is subjected to decanter separation conditions effective to produce a first washed APC decanter aqueous phase and a first washed APC decanter organic phase. The first washed APC decanter organic phase is subjected to a second wash with water to remove trace alkali base, producing a twice washed APC decanter organic stream. The twice washed APC decanter organic stream is again separated into a final washed APC organic phase comprising the "MDC feed" and a final washed APC decanter aqueous phase.

The MDC feed comprises MEK, hydrocarbon, water, and other organic species. The MDC feed is fed to a distillation column, called a MEK Dehydration Column or "MDC" and subjected to MDC conditions effective to produce a MDC overhead comprising water and organic species having a boiling point sufficiently lower than MEK to be separated from the MEK, and a MDC bottoms comprising MEK. Organic species having a boiling point sufficiently lower than MEK include, but are not necessarily limited to methanol and ethanol.

In a preferred embodiment, the MDC conditions comprise feeding an entrainer to the MDC to remove the water from the MDC feed with minimal loss of MEK in the MDC overhead. In a preferred embodiment, the entrainer is selected from the group consisting of hexane, cyclohexane, heptane, and combinations thereof. A most preferred entrainer is cyclohexane.

In addition to MEK, the MDC bottoms generally comprises hydrocarbon and other organic species having a boiling point which is the same as or greater than MEK. The remaining procedures are the same as described in the corresponding sections under the heading "Where cumene is not fed to the reaction mixture," above.

The application will be better understood with reference to the following examples:

EXAMPLE 1

Batch oxidations were performed to measure the effect of reaction temperature on conversion vs. time and selectivity. Hydrocarbon mixtures having a weight ratio of s-butyl benzene to cumene of 7 to 1 were oxidized using depleted air with 7 vol. % oxygen at atmospheric pressure. The results, presented in the following Tables, were measured using gas chromatography. The Table 1A reflects results at 110° C.:

TABLE 1A

| Temperature 110° C. | Compositions in Weight % | | | | | |
|---|---|---|---|---|---|---|
| Time, hours | 2 | 4 | 6 | 8 | 10 | 12 |
| Cumene | 11.99 | 11.83 | 11.46 | 10.95 | 10.33 | 9.96 |
| s-BBenzene* | 85.37 | 85.51 | 84.52 | 82.69 | 80.10 | 79.33 |
| AP** | 0.03 | 0.05 | 0.08 | 0.12 | 0.21 | 0.32 |
| DMBA | 0.14 | 0.15 | 0.17 | 0.19 | 0.22 | 0.27 |
| EMBA | 0.01 | 0.03 | 0.07 | 0.05 | 0.09 | 0.11 |
| CHP*** | 0.75 | 0.96 | 1.28 | 1.62 | 2.25 | 2.69 |
| sBBHP**** | 0.41 | 1.03 | 1.96 | 3.15 | 5.02 | 6.63 |
| Unknowns | 0.10 | 0.12 | 0.14 | 0.18 | 0.23 | 0.35 |

*s-butylbenzene
**acetophenone
***cumene hydroperoxide
****s-butylbenzene hydroperoxide Table 1B reflects results at 125° C.

TABLE 1B

| Temperature 125° C. | Compositions in Weight % | | | | | |
|---|---|---|---|---|---|---|
| Time, hours | 1 | 2 | 3 | 4 | 5 | 6 |
| Cumene | 12.13 | 11.69 | 11.10 | 10.26 | 10.06 | 9.55 |
| s-BBenzene | 85.90 | 84.11 | 81.53 | 78.30 | 77.61 | 76.26 |
| AP | 0.06 | 0.12 | 0.24 | 0.49 | 0.60 | 0.96 |
| DMBA | 0.11 | 0.14 | 0.19 | 0.29 | 0.34 | 0.46 |
| EMBA | 0.01 | 0.02 | 0.06 | 0.15 | 0.24 | 0.30 |
| CHP | 0.98 | 1.27 | 1.69 | 2.33 | 2.65 | 3.23 |
| sBBHP | 0.81 | 1.90 | 3.41 | 5.82 | 6.95 | 9.32 |
| Unknowns | 0.10 | 0.11 | 0.16 | 0.37 | 0.46 | 0.69 |

The foregoing results indicate that, when the reaction temperature was increased by 15° C., the reaction time to achieve a given total hydroperoxide conversion was about halved.

EXAMPLE 2

A standard oxidation mixture was prepared containing 300 grams of sec-butyl benzene (sBB), and an amount of cumene effective to produce a weight ratio of sBB:cumene of 3.4:1. The oxidation mixture also contained 1% cumene hydroperoxide as an initiator. The oxidation mixture was exposed to oxidation conditions comprising a temperature of 130° C., an oxidizing agent comprising 500 cc/min. 7% $O_2$ in $N_2$, and a steady pressure of 40 psig. All experiments were carried out in a 500 cc Buchi Type II reactor, with stirring rate of 1300 rpm.

The foregoing standard oxidation mixture was oxidized as a control to assess the effect of ammonia on the reaction. No ammonia or water was added to the control mixture. After 8 hours, the mixture contained 438 wppm formic acid, 860 wppm acetic acid, and 1510 wppm phenol.

In a first comparative experiment, during oxidation, gaseous $NH_3$ was bubbled through the standard oxidation mixture at a weight ratio of 9.2:1 based on the expected acid production, resulting in an ammonia feed rate of 3.26 cc/min.

In a second comparative experiment, 1.25 wt. % water was charged with the standard oxidation mixture. During oxidation, gaseous ammonia was bubbled through the oxidation mixture in an amount sufficient to neutralize 73% of the expected acid production (molar ratio of $NH_3$ of 0.73:1 based on the expected acid production), resulting in feed rate of ammonia of 0.26 cc/min.

Measurements of cumene hydroperoxide (CHP), s-butylbenzene hydroperoxide (sBBHP), acetophenone (AP), DMBA, and EMBA were performed on samples taken every two hours from the control mixture, and every hour from the comparative experimental mixtures, with the following results:

TABLE 2a

| | Oxidation without $NH_3$ | | | | |
|---|---|---|---|---|---|
| Time (hour) | 1 | 2 | 4 | 6 | 8 |
| CHP | 2.3 | 3.1 | 5.2 | 7.0 | 7.7 |
| sBBHP | 1.3 | 3.5 | 7.1 | 10.3 | 12.1 |
| AP | 0.1 | 0.3 | 0.8 | 1.7 | 3.1 |
| DMBA | 0.3 | 0.3 | 0.7 | 1.3 | 2.3 |
| ENBA | 0.1 | 0.1 | 0.2 | 0.6 | 1.2 |

TABLE 2b

Oxidation with $NH_3$
with 9.2:1 $NH_3$ to expected acid amount
Ammonia feed rate = 3.26 cc/min

| Time (hour) | 1 | 2 | 3 | 4 | 5 | 6 | 7 | 8 |
|---|---|---|---|---|---|---|---|---|
| CHP | 2.0 | 3.1 | 4.4 | 5.5 | 6.4 | 7.0 | 7.5 | 7.6 |
| sBBHP | 1.8 | 3.7 | 5.9 | 7.8 | 9.5 | 11.0 | 12.1 | 12.7 |
| AP | 0.1 | 0.3 | 0.5 | 0.8 | 1.2 | 1.8 | 2.6 | 3.5 |
| DMBA | 0.2 | 0.3 | 0.5 | 0.6 | 0.9 | 1.3 | 1.8 | 2.4 |
| EMBA | 0.0 | 0.1 | 0.1 | 0.2 | 0.4 | 0.6 | 0.9 | 1.3 |

TABLE 2c

Oxidation with 1.25%
$H_2O$ and $NH_3$ at 0.73:1 $NH_3$ to
expected acid amount
Ammionia feed rate = 0.26 cc/min

| Time (hour) | 1 | 2 | 3 | 4 | 5 | 6 | 7 | 8 |
|---|---|---|---|---|---|---|---|---|
| CHP | 2.1 | 3.2 | 4.5 | 5.6 | 6.6 | 7.4 | 8.1 | 8.5 |
| sBBHP | 2.0 | 3.7 | 5.8 | 7.8 | 9.7 | 11.4 | 12.9 | 14.0 |
| AP | 0.1 | 0.3 | 0.5 | 0.8 | 1.2 | 1.8 | 2.6 | 3.4 |
| DMBA | 0.2 | 0.3 | 0.4 | 0.6 | 0.9 | 1.3 | 1.8 | 2.3 |
| EMBA | 0.0 | 0.1 | 0.1 | 0.2 | 0.4 | 0.6 | 0.9 | 1.2 |

Figure 3:
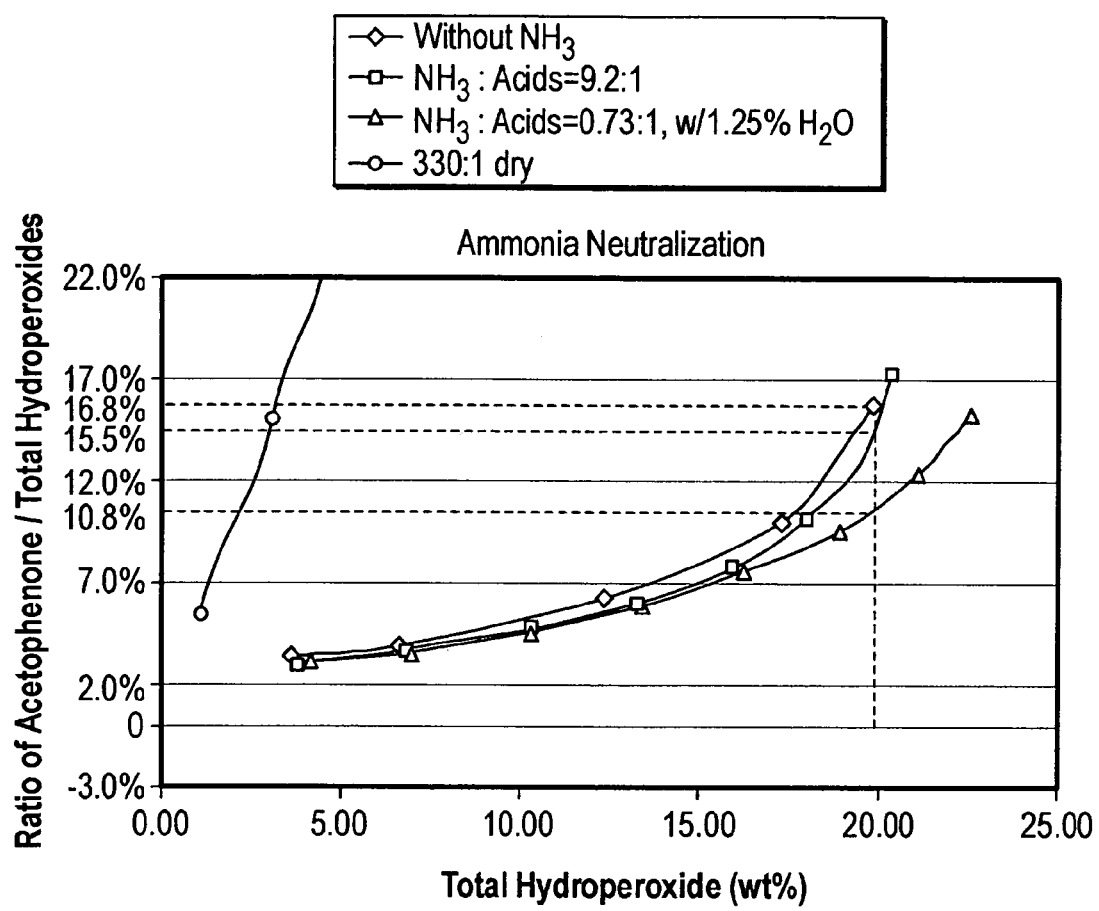
FIG. 3 is a chart of the ratio of acetophenone to total hydroperoxides achieved in a control with no added $NH_3$, in experimental samples to which $NH_3$ was added as described in Example 2, and in a sample to which dry $NH_3$ was added at a ratio of 330:1 based on expected acid production.

The improvements are summarized in the following Table, and illustrated in FIG. 3:

Summary of Improvement as a Result of $NH_3$ Addition:

| Compare w/ no $NH_3$ base case | HP yield | AP* | (DNBA + EMBA)* | Phenol |
|---|---|---|---|---|
| NH3:acids = 9.2:1, no water | +2.3% | −7.70% | −12.4% | −32.9% |
| NH3:acids = 0.73:1, w/ 1.25% water | +13.5% | −35.70% | −37.2% | −73.4% |

*measured at total hydroperoxide level of 19.82%

Figure 4:
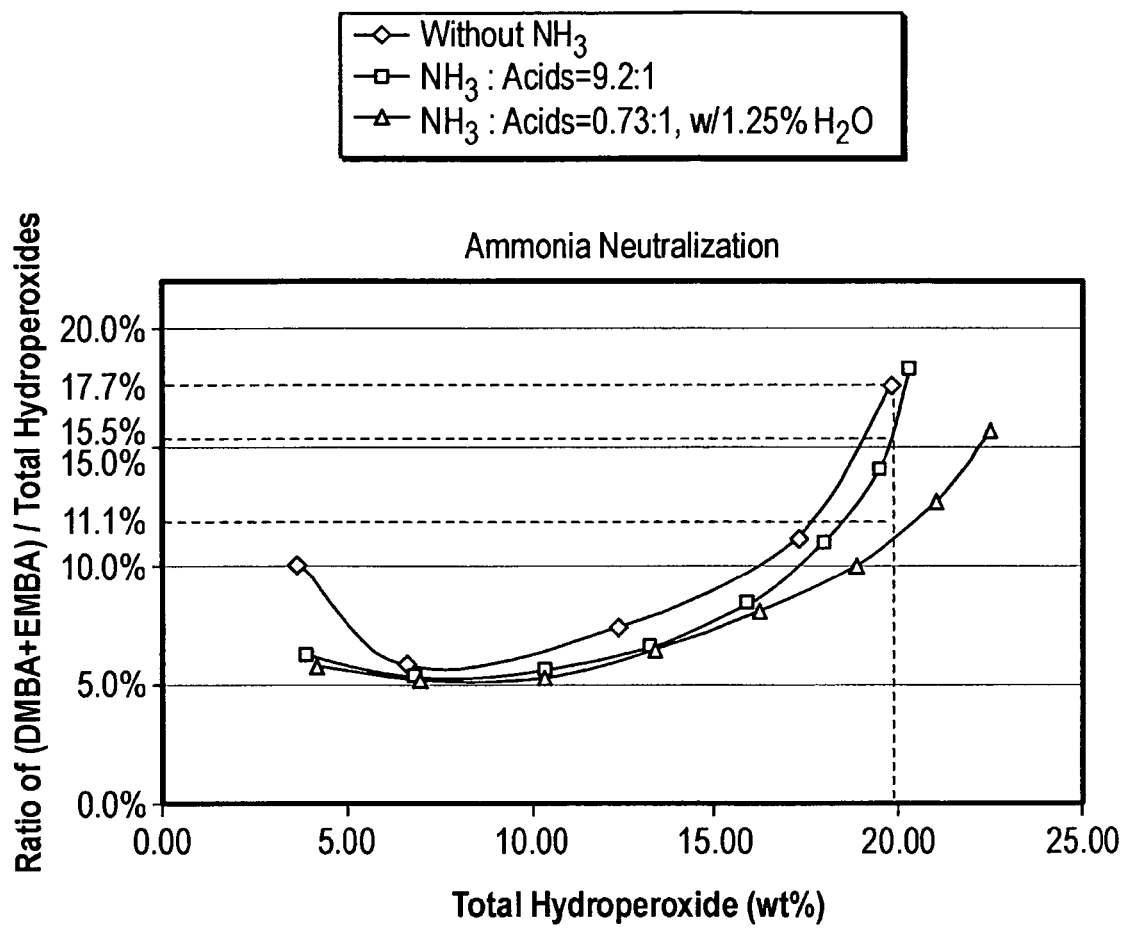
FIG. 4 is a chart of the ratio of (DMBA+EMBA) to total hydroperoxides achieved in a control with no added $NH_3$ and in experimental samples to which $NH_3$ was added, as described in Example 2.
Figure 5:
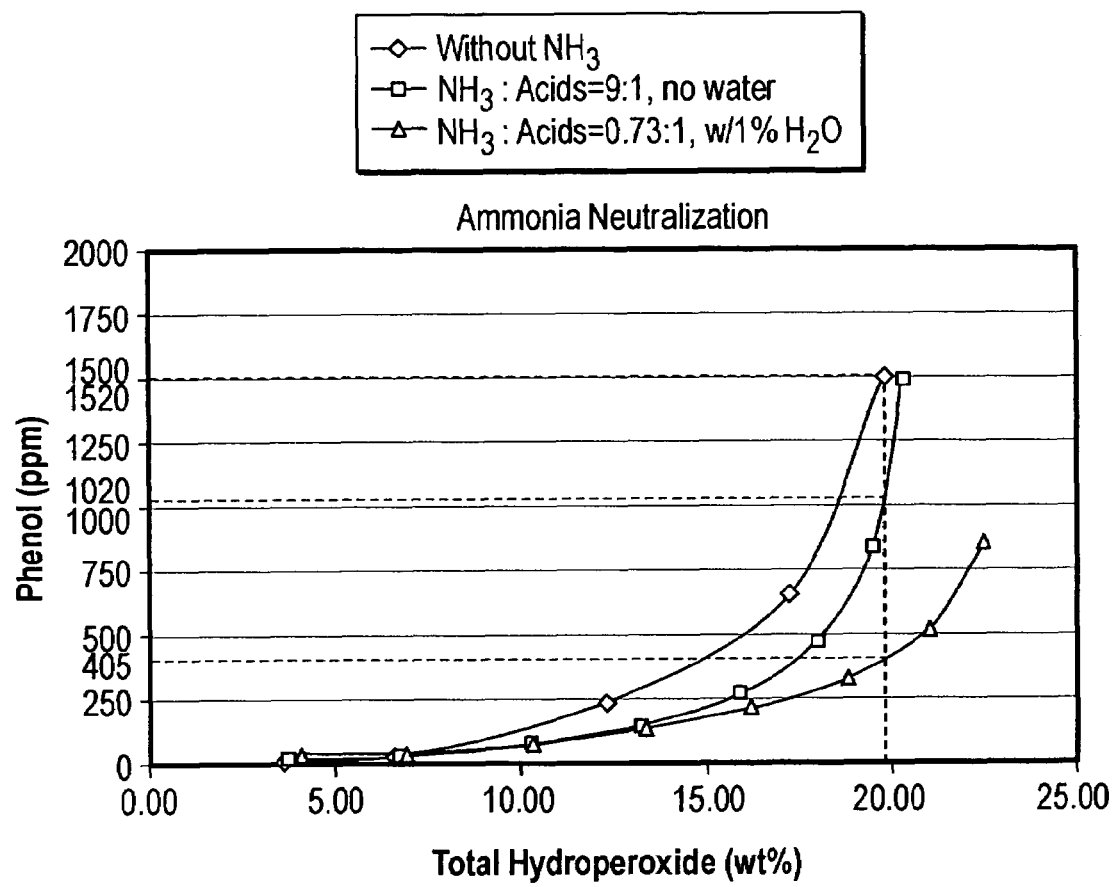
FIG. 5 is a chart of the ratio of phenol to total hydroperoxides achieved in a control with no added $NH_3$ and in experimental samples to which $NH_3$ was added, as described in Example 2.

After 8 hours, the hydroperoxide yield in the oxidation mixture charged with ammonia was 13.5% higher than in the control and phenol poison was 44% lower than in the control. After each oxidation mixture had reached 20 w % hydroperoxides, the ammonia-charged oxidation mixture exhibited an AP production 36% lower than in the control and DMBA and EMBA were 37% lower than in the control. The results are graphically depicted in FIGS. 3-5. Note that FIG. 3 also includes the results when dry $NH_3$ was added at a ratio of 330:1 based on expected acid production. In this experiment, AP was higher than in the control.

Persons of ordinary skill in the art will recognize that many modifications may be made to the foregoing without departing from the spirit and scope thereof. The embodiment described herein is meant to be illustrative only and should not be taken as limiting the invention, which is defined in the following claims.

We claim:

1. A process for producing controllable yields of a combination of products selected from the group consisting of (a) phenol and methyl ethyl ketone (MEK) and (b) phenol, acetone, and MEK, said process comprising:
   feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene;
   exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
   cleaving the product hydroperoxides under cleavage conditions effective to produce a cleavage product comprising a combination selected from the group consisting of (a) phenol and MEK, and (b) phenol, acetone, and MEK; and,
   separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
   recovering one or more products selected from the group consisting of (a) an MEK product and (b) a combination comprising an MEK product and an acetone product,
   wherein said oxidation conditions comprise feeding said oxidation mixture to a series of continuous oxidation reactors and feeding a source of molecular oxygen to the oxidation mixture.

2. The process of claim 1 further comprising separating the oxidation product stream under oxidation separation conditions effective to produce an oxidation bottoms (OB) and an oxidation vapor overhead.

3. The process of claim 2 wherein the oxidation conditions are effective to produce an oxidation product stream further comprising:
   major byproducts selected from the group consisting of acetophenone, di-methyl benzyl carbinol (DMBA), and ethyl methyl benzyl carbinol (EMBA), and combinations thereof; and
   minor by-products selected from the group consisting of di-cumyl peroxide, di-s-butylperoxide, cumyl s-butyl peroxide, formic acid, acetic acid, methanol, ethanol, methyl hydroperoxide, ethyl hydroperoxide, phenol, acetone, and MEK, and combinations thereof.

4. The process of claim 2 wherein the weight ratio of cumene to s-butylbenzene is from about 1:8 (or 12.5 wt. % cumene) to about 2:1 (or about 66.7 wt. % cumene).

5. A process for producing controllable yields of a combination of products selected from the group consisting of (a) phenol and methyl ethyl ketone (MEK) and (b) phenol, acetone, and MEK, said process comprising:
   feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene:
   exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
   cleaving the product hydroperoxides under cleavage conditions effective to produce a cleavage product comprising a combination selected from the group consisting of (a) phenol and MEK, and (b) phenol, acetone, and MEK; and,
   separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
   recovering one or more products selected from the group consisting of (a) an MEK product and (b) a combination comprising an MEK product and an acetone product,
   wherein the oxidation reactor is a batch oxidation reactor and the oxidation conditions comprise:
   an oxidation temperature of from about 90° C. to about 150° C.;
   an oxidation pressure of from about 0 psig to about 100 psig; and,
   an oxidation reaction time of from about 6 to about 11 hours.

6. The process of claim 5 wherein the oxidation pressure is from about 15 psig to about 40 psig.

7. The process of claim 2 wherein the oxidation conditions comprise:
   an oxidation temperature of from about 100° C. to about 130° C.;
   an oxidation pressure of from about 0 psig to about 100 psig; and,
   a total residence time in each continuous reactor of from about 1 to about 5 hours.

8. The process of claim 7 wherein the oxidation pressure is from about 15 psig to about 40 psig.

9. The process of claim 2 wherein the oxidation conditions are effective to produce about 5% or more conversion to the product hydroperoxides.

10. The process of claim 2 wherein the oxidation conditions are effective to produce from about 10% to about 30% conversion to the product hydroperoxides.

11. The process of claim 2 wherein the oxidation conditions are effective to produce from about 15% to about 25% conversion to the product hydroperoxides.

12. The process of claim 2 wherein the series of continuous oxidation reactors comprises from about 3 to about 8 continuous reactors in series.

13. The process of claim 8 wherein the series of continuous oxidation reactors comprises from about 3 to about 8 continuous reactors in series.

14. The process of claim 2 wherein the weight ratio of cumene to s-butyl benzene is 2:1, and the series of continuous oxidation reactors are 4 continuous oxidation reactors in series.

15. The process of claim 2 wherein the weight ratio of cumene to s-butylbenzene is 1:8 and the series of continuous oxidation reactors are from 5 to 6 continuous oxidation reactors in series.

16. The process of claim 2 further comprising cooling the oxidation vapor overhead and the oxidation reaction mixture.

17. The process of claim 16 wherein said cooling comprises exchanging heat between the oxidation mixture and cooling fluids.

18. The process of claim 17 further comprising recirculating the oxidation mixture to heat exchangers external to the one or more oxidation reactors.

19. The process of claim 16 further comprising:
separating the oxidation vapor overhead into an oxidation vapor overhead-organic fraction (OVO-OF) and an oxidation vapor overhead aqueous fraction (OVO-AF);
decomposing the OVO-AF under thermal decomposition conditions effective to decompose ethyl hydroperoxide and methyl hydroperoxide to produce a thermal decomposition product comprising alcohols, aldehydes, carboxylic acids, and combinations thereof, said thermal decomposition conditions comprising a thermal decomposition temperature of from about 80° C. to 250° C. and a thermal decomposition pressure of from about 100 psig to about 200 psig.

20. The process of claim 16 further comprising
separating the oxidation vapor overhead into an oxidation vapor overhead organic fraction ("OVO-OF") and an oxidation vapor overhead aqueous fraction ("OVO-AR");
decomposing the OVO-AF under thermal decomposition conditions effective to decompose ethyl hydroperoxide and methyl hydroperoxide to produce a thermal decomposition product comprising alcohols, aldehydes, carboxylic acids, and combinations thereof, said thermal decomposition conditions comprising adding an OVO-AF inorganic acid to the OVO-AF under conditions effective to accelerate the decomposition and neutralizing the OVO-AF inorganic acid with an OVO-AF alkali base having a pH of from about 10 to about 11; and,
distilling the thermal decomposition product under thermal decomposition product distillation conditions (TDP-distillation conditions) comprising a TDP-distillation temperature effective to remove organic species other than carboxylic acids from the first decomposition product, said TDP-distillation conditions being effective to produce a thermal decomposition product organic distillate and a thermal decomposition product aqueous bottoms.

21. The process of claim 20 wherein the OVO-AF inorganic acid is selected from the group consisting of sulfuric acid, hydrochloric acid, and phosphoric acid.

22. The process of claim 20 wherein the OVO-AF inorganic acid is sulfuric acid.

23. The process of claim 22 wherein the OVO-AF inorganic acid is added to a concentration of from about 20 ppm to about 100 ppm in the OVO-AF.

24. The process of claim 23 further comprising neutralizing the OVO-AF inorganic acid with an OVO-AF base selected from the group consisting of sodium carbonate and sodium hydroxide.

25. The process of claim 2 further comprising feeding the OB and a quantity of water to one or more strippers and exposing the OB to stripping conditions effective to concentrate but ineffective to decompose hydroperoxides selected from the group consisting of s-butylbenzene hydroperoxide, cumene hydroperoxide, and combinations thereof, the stripping conditions being effective to produce a stripper overhead and a stripper bottoms comprising the hydroperoxides, said quantity of water being effective to produce a first condenser vapor phase comprising a majority of water, ethanol, methanol, methyl hydroperoxide, ethyl hydroperoxide, and combinations thereof, in the first stripper overhead.

26. The process of claim 25 wherein said quantity of water is equivalent to from about 0.1 wt. % to about 1.5 wt. % of the oxidation bottoms.

27. The process of claim 4 further comprising feeding the OB and a quantity of water to one or more strippers and exposing the OB to stripping conditions effective to concentrate but ineffective to decompose hydroperoxides selected from the group consisting of s-butylbenzene hydroperoxide, cumene hydroperoxide, and combinations thereof, the stripping conditions being effective to produce a stripper overhead and a stripper bottoms comprising the hydroperoxides, said quantity of water being effective to produce a first condenser vapor phase comprising a majority of water, ethanol, methanol, methyl hydroperoxide, ethyl hydroperoxide, and combinations thereof, in the first stripper overhead.

28. The process of claim 27 wherein said quantity of water is equivalent to from about 0.1 wt. % to about 1.5 wt. % of the oxidation bottoms.

29. The process of claim 7 further comprising feeding the OB and a quantity of water to one or more strippers and exposing the OB to stripping conditions effective to concentrate but ineffective to decompose hydroperoxides selected from the group consisting of s-butylbenzene hydroperoxide, cumene hydroperoxide, and combinations thereof, the stripping conditions being effective to produce a stripper overhead and a stripper bottoms comprising the hydroperoxides, said quantity of water being effective to produce a first condenser vapor phase comprising a majority of water, ethanol, methanol, methyl hydroperoxide, ethyl hydroperoxide, and combinations thereof, in the first stripper overhead.

30. The process of claim 29 wherein said quantity of water is equivalent to from about 0.1 wt. % to about 1.5 wt. % of the oxidation bottoms.

31. The process of claim 25 wherein the stripper overhead comprises unreacted hydrocarbon, dissolved water, and organic species having a boiling point lower than s-butybenzene hydroperoxide selected from the group consisting of minor by-products, DMBA, EMBA, acetophenone, and combinations thereof.

32. The process of claim 31 wherein the stripping conditions comprise a stripper bottoms temperature of about 120° C. or less.

33. The process of claim 32 further comprising feeding the OB through multiple strippers.

34. The process of claim 33 wherein the multiple strippers comprise three strippers in series.

35. The process of claim 34 wherein the stripping conditions comprise
first stripper conditions effective to produce a first stripper bottoms and a first stripper overhead comprising a portion of the one or more alkylbenzenes in the OB,
second stripper conditions effective to produce a second stripper overhead and a second stripper bottoms, and
third stripper conditions effective to produce a third stripper overhead and third stripper bottoms,
wherein said stripping conditions comprise a first stripper pressure greater than a second stripper pressure greater than a third stripper pressure.

36. The process of claim 35 wherein
said first stripper pressure is from about 40 to about 60 mm Hg;
said second stripper pressure is from about 25 to about 35 mm Hg; and,
said third stripper pressure is from about 10 to about 20 mm Hg.

37. The process of claim 35 wherein
said first stripper pressure is about 50 mm Hg;
said second stripper pressure is about 30 mm Hg; and,
said third stripper pressure is about 15 mm Hg.

38. The process of claim 35 wherein the first stripper conditions are effective to produce a first stripper overhead comprising:
99 wt. % or more of the water fed with the OB;
99 wt. % or more of methanol in the OB;
99 wt. % or more of ethanol in the OB;
99 wt. % or more of methyl hydroperoxide in the OB; and,
99 wt. % or more of ethyl hydroperoxide in the OB.

39. The process of claim 35 wherein the first stripper conditions are effective to produce a first stripper overhead comprising:
all water fed with the OB;
all methanol in the OB;
all ethanol in the OB;
all methyl hydroperoxide in the OB;
all ethyl hydroperoxide in the OB.

40. The process of claim 35 further comprising exposing the first stripper overhead to first stripper overhead condenser conditions comprising a first stripper overhead condensation temperature and a first stripper overhead condensation pressure, said first stripper overhead condenser conditions being effective to cause a majority of the one or more alkylbenzenes in the first stripper overhead to condense, producing a first condenser organic phase, said first stripper overhead condenser conditions and said quantity of water also being effective to produce a first condenser vapor phase comprising a majority of water, ethanol, methanol, methyl hydroperoxide, ethyl hydroperoxide, and combinations thereof, in the first stripper overhead.

41. The process of claim 40 wherein the first condenser organic phase comprises:
about 90 wt. % or more of the s-butylbenzene in the first stripper overhead; and,
if present, about 85 wt. % or more of cumene in the first stripper overhead.

42. The process of claim 41 wherein the first stripper overhead condensation temperature and the first stripper overhead condensation pressure are effective to produce a first condenser vapor phase comprising about 95 wt. % or more of each of the water, the ethanol, the methanol, the methyl hydroperoxide, the ethyl hydroperoxide, and combinations thereof, in the first stripper overhead.

43. The process of claim 42 further comprising subjecting the first condenser vapor phase to second condensation conditions effective to form a second condenser organic phase and a second condenser aqueous phase comprising a majority of each of the ethanol, the methanol, the methyl hydroperoxide, the ethyl hydroperoxide in the first condenser vapor phase, and combinations thereof.

44. The process of claim 43 further comprising subjecting the second condenser aqueous phase to said decomposition conditions, producing a decomposition product comprising alcohols, aldehydes, carboxylic acids, and combinations thereof.

45. The process of claim 35 further comprising recycling greater than about 90 wt. % of the hydrocarbons in the OB to the oxidation mixture.

46. A process for producing controllable yields of a combination of products selected from the group consisting of (a) phenol and methyl ethyl ketone (MEK) and (b) phenol, acetone, and MEK, said process comprising:
feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene;
exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
cleaving the product hydroperoxides under cleavage conditions effective to produce a cleavage product comprising a combination selected from the group consisting of (a) phenol and MEK, and (b) phenol, acetone, and MEK; and,
separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
recovering one or more products selected from the group consisting of (a) an MEK product and (b) a combination comprising an MEK product and an acetone product,
wherein said cleaving comprises:
feeding a cleavage reaction feed to a cleavage reactor to produce a cleavage reaction mixture comprising the one or more hydroperoxides; and
subjecting the cleavage reaction mixture to cleavage reaction conditions effective to produce a cleavage reaction product comprising phenol and one or more component selected from the group consisting of methyl ethyl ketone, acetone, and combinations thereof;
wherein the cleavage reaction conditions comprise a cleavage reaction temperature which is sufficiently high to cleave a majority of the one or more hydroperoxides but sufficiently low to produce a first quantity of non-recoverable byproducts from components selected from the group consisting of DMBA, EMBA, and combinations thereof, the first quantity of the non-recoverable by-products being less than a second quantity of the non-recoverable byproducts produced by the same process at a cleavage reaction temperature of 75° C. or higher.

47. The process of claim 46 wherein said cleaving further comprises:
feeding to a first cleavage reactor a first cleavage reaction feed comprising at least a portion of the third stripper bottoms and an acid catalyst effective to catalyze the cleavage of hydroperoxides selected from the group consisting of s-butylbenzene hydroperoxide, cumene hydroperoxide, and combinations thereof, the first cleavage reaction conditions being effective to produce a first cleavage reaction mixture comprising a first cleavage reaction product; and,
feeding the first cleavage reaction product to a second cleavage reactor to produce a second cleavage reaction mixture and subjecting the second cleavage reaction mixture to second cleavage reaction conditions effective to produce a second cleavage reaction product, said second cleavage reaction conditions comprise a second cleavage reaction temperature effective to convert DMBA to α-methyl styrene (AMS) and to convert EMBA to a compound selected from the group consisting of α-ethyl styrene (AES), 2-phenyl-2-butene (2P2B), and combinations thereof.

48. The process of claim 46 wherein the cleavage reaction feed is a first cleavage reaction feed to a first cleavage reactor, and the cleavage conditions comprise first cleavage reaction conditions effective to produce a first cleavage reaction mixture comprising a first cleavage reaction product, said process further comprising feeding the first cleavage reaction product to a second cleavage reactor to produce a second cleavage reaction mixture and subjecting the second cleavage reaction mixture to second cleavage reaction conditions effective to produce a second cleavage reaction product, said second cleavage reaction conditions comprising a second cleavage reaction temperature effective to convert DMBA to α-methyl styrene and to convert EMBA to a compound selected from the group consisting of α-ethyl styrene (AES), 2-phenyl-2-butene (2P2B), and combinations thereof.

49. The process of claim 47 wherein the first cleavage reactor and the second cleavage reactor are selected from the group consisting of plug-flow reactors (PFR's), plug-flow reactors with recycle (PFRR's), and continuous stirred tank reactors (CSTR's).

50. The process of claim 47 wherein the first cleavage reactor is a stirred tank reactor comprising internal or external heat exchangers effective to maintain the first cleavage reaction mixture at the first cleavage reaction temperature.

51. The process of claim 47 wherein the first cleavage reactor is a PFRR comprising one or more heat exchangers effective to maintain the first cleavage reaction mixture at the first cleavage reaction temperature.

52. The process of claim 47 wherein the first cleavage reaction conditions comprise:
a first cleavage reaction temperature of from about 45° C. to about 70° C.; and,
a first cleavage reaction pressure sufficiently high to maintain the first cleavage reaction mixture in the liquid phase.

53. The process of claim 52 wherein the first cleavage reaction temperature is from about 450° C. to about 600° C.

54. The process of claim 47 wherein the first cleavage reaction conditions comprise
a first cleavage reaction temperature is from about 45° C. to about 55° C.; and,
a first cleavage reaction pressure is about 0.5 atmospheres or more.

55. The process of claim 52 wherein the first cleavage reaction conditions comprise recirculating a recycle flow of the first cleavage reaction mixture through the first cleavage reactor.

56. The process of claim 55 further comprising withdrawing the first cleavage reaction product from the first cleavage reactor upstream of the first cleavage reactor feed.

57. The process of claim 55 wherein the recycle flow through the first cleavage reactor is greater than the first cleavage reactor feed flow.

58. The process of claim 55 wherein the ratio of the recycle flow through the first cleavage reactor compared to the first cleavage reactor feed flow is from about 10:1 to about 100:1 on a weight basis.

59. The process of claim 55 wherein the ratio of the recycle flow through the first cleavage reactor compared to the first cleavage reactor feed flow is from about 20:1 to 40:1 on a weight basis.

60. The process of claim 57 wherein the first cleavage reaction conditions comprise a first cleavage reaction residence time effective to cleave:
about 95% or more of s-butylbenzene hydroperoxide in the first cleavage reaction mixture to phenol and MEK; and,
if present, about 95% or more of cumene hydroperoxide in the first cleavage reaction mixture to phenol and acetone.

61. The process of claim 59 wherein the first cleavage reaction residence time is from about 1 minute to about 10 minutes.

62. The process of claim 57 wherein the acid catalyst is selected from the group consisting of sulfuric acid, sulfuric acid anhydride, perchloric acid, phosphoric acid, and combinations thereof.

63. The process of claim 57 wherein the acid catalyst comprises sulfuric acid.

64. The process of claim 57 further comprising adding the acid catalyst to a first cleavage reaction mixture side stream at one or more acid addition points and withdrawing the first cleavage reaction mixture side stream between the first cleavage reaction product withdrawal point and the first cleavage reactor feed point.

65. The process of claim 64 wherein the amount of acid catalyst fed to the first cleavage reactor is from about 0.005% to about 0.1% by weight based on the first cleavage reactor feed flow.

66. The process of claim 57 wherein the second cleavage reactor comprises a once through plug flow reactor.

67. The process of claim 65 wherein the second cleavage reactor comprises a once through plug flow reactor.

68. The process of claim 57 wherein the second cleavage reaction conditions comprise a second cleavage reaction temperature and a second cleavage reaction residence time effective to cleave 95 wt. % or more of the hydroperoxides in the second cleavage reaction mixture.

69. The process of claim 68 wherein the second cleavage reaction conditions are effective to convert:
75 wt. % or more of DMBA in the first cleavage reaction product to AMS; and
75 wt. % or more of EMBA in the first cleavage reaction product to a compound selected from the group consisting of AES, 2P2B, and combinations thereof.

70. The process of claim 68 wherein the second cleavage reaction conditions are effective to convert:
85 wt. % or more of DMBA in the first cleavage reaction product to AMS; and 85 wt. % or more of EMBA in the first cleavage reaction product to a compound selected from the group consisting of AES, 2P2B, and combinations thereof.

71. The process of claim 57 wherein the second cleavage reaction conditions comprise:
a second cleavage reaction temperature of from about 60° C. to about 130° C.; and
a second cleavage reaction pressure which, when combined with the second cleavage reaction temperature, is sufficient to maintain the second cleavage reaction mixture in the liquid phase; and,
a second cleavage reaction residence time of from about 5 seconds to about 1 minute.

72. The process of claim 57 wherein
the second cleavage reaction temperature is from about 70° C. to about 120° C.; and,
the second cleavage reaction pressure is about 30 psig or more.

73. The process of claim 69 further comprising taking multiple exotherm measurements to verify the rate of the cleavage reaction.

74. The process of claim 73 further comprising controlling the amount of acid catalyst added to the first cleavage reaction mixture based on the multiple exotherm measurements.

75. The process of claim 73 wherein taking the multiple exotherm measurements comprises:
taking a first reaction mixture side stream exotherm measurement;
taking a first cleavage reactor (FCR) exotherm measurement; and,
taking a second cleavage reactor (SCR) exotherm measurement.

76. The process of claim 69 further comprising
cooling and neutralizing the second cleavage reaction product with an amount of a second cleavage reaction product neutralizing base under second cleavage reaction product neutralization conditions effective to produce a neutralized second cleavage reaction product, the second cleavage reaction product neutralization conditions comprising a second cleavage reaction product neutralization pressure sufficient to maintain the second cleavage reaction product in the liquid phase; and,
separating the neutralized second cleavage reaction product into a neutralized second cleavage reaction product aqueous fraction and a CKC feed comprising a neutralized second cleavage reaction product organic fraction.

77. The process of claim 76 wherein the second cleavage reaction product neutralization conditions comprise
a temperature of from about 40° C. to about 60° C.; and,
a second cleavage reaction pressure which, when combined with the second cleavage reaction temperature, is sufficient to maintain the second cleavage reaction mixture in the liquid phase.

78. The process of claim 77 wherein the second cleavage reaction product neutralization temperature is from about 45° C. to about 50° C.

79. The process of claim 78 wherein said amount of second cleavage reaction product neutralizing base comprises an amount of alkali base, said amount being effective to maintain the neutralized second cleavage reaction product aqueous fraction at a pH of from about 5 to about 11.

80. The process of claim 78 wherein said amount of second cleavage reaction product neutralizing base is effective to maintain the neutralized second cleavage reaction product aqueous fraction at a pH of from about 5 to about 5.5.

81. The process of claim 78 wherein the second cleavage reaction product neutralizing base comprises an alkali base selected from the group consisting of hydroxides, carbonates, bicarbonates, and phenates of sodium, potassium, and lithium, and combinations thereof.

82. The process of claim 78 wherein the weight ratio of the CKC feed to the neutralized second cleavage reaction product aqueous fraction is from about 1:3 to about 3:1.

83. The process of claim 82 further comprising circulating at least part of the neutralized second cleavage reaction product aqueous fraction back to a neutralization apparatus.

84. The process of claim 82 further comprising maintaining the salt concentration in the neutralized second cleavage reaction product aqueous fraction at from about 1 to about 30% by weight.

85. A process for producing controllable yields of a combination of products selected from the group consisting of (a) phenol and methyl ethyl ketone (MEK) and (b) phenol, acetone, and MEK, said process comprising:
feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene;
exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
cleaving the product hydroperoxides under cleavage conditions effective to produce a cleavage product comprising a combination selected from the group consisting of (a) phenol and MEK, and (b) phenol, acetone, and MEK; and,
separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
recovering one or more products selected from the group consisting of (a) an MEK product and (b) a combination comprising an MEK product and an acetone product,
further comprising feeding a CKC feed comprising a neutralized organic fraction from said cleavage product to a cleavage product separation zone and exposing the CKC feed to CKC conditions effective to produce
a crude phenol fraction comprising from about 2 wt. % to about 5 wt. % of a combination of the one or more alkylbenzenes, AMS, AES, and 2P2B; and,
a CKC vapor distillate comprising most of the water, the one or more alkylbenzenes, AMS, AES, 2P2B, and combinations thereof in the CKC feed.

86. The process of claim 85 wherein the CKC conditions are effective to produce a CKC vapor distillate comprising 99 wt. % or more of water in the CKC feed and 75% or more of the hydroxy-ketones in the CKC feed.

87. The process of claim 85 wherein the CKC conditions are effective to produce a CKC vapor distillate comprising all water in the CKC feed.

88. The process of claim 85 wherein the CKC conditions comprise
a CKC top temperature of from about 190° C. to about 220° C.;
a CKC top pressure of from about 0 psig to about 10 psig; and,
a minimum mass reflux ratio of about 0.05/1.

89. The process of claim 85 wherein the CKC conditions comprise
a CKC top temperature of from about 203° C. to 207° C.;
a CKC top pressure of from about 3 psig to about 7 psig; and,
a mass reflux ratio of from about 0.1/1 to about 0.2/1.

90. The process of claim 85 further comprising
condensing the CKC vapor distillate to produce a CKC vapor condensate, said condensing comprising feeding the CKC vapor distillate to a CKC vapor condenser and subjecting the CKC vapor distillate to CKC vapor condenser conditions effective to produce the CKC vapor condensate; and,
exposing the CKC vapor condensate to CKC vapor condensate separation conditions effective to produce a CKC vapor condensate organic layer and a CKC vapor condensate aqueous layer.

91. The process of claim 90 further comprising feeding a CKC recycle portion of the CKC vapor condensate aqueous layer to the CKC column at a recycle point.

92. The process of claim 91 wherein the recycle point is the same tray at which the CKC feed is fed to the CKC column.

93. The process of claim 92 wherein the CKC recycle portion comprises from about 50 wt. % to 95 wt. % of the CKC vapor condensate aqueous layer.

94. The process of claim 92 wherein the CKC recycle portion comprises from about 75 wt. % to about 80 wt. % of the CKC vapor condensate aqueous layer.

95. The process of claim 91 further comprising mixing a remainder of the CKC vapor condensate aqueous layer with the CKC vapor condensate organic layer to form a CKC vapor condensate mixture comprising 2 wt. % phenol or less.

96. The process of claim 95 wherein the CKC vapor condensate mixture comprises about 1 wt. % phenol or less.

97. The process of claim 85 further comprising feeding a CKC vapor condensate mixture from said CKC feed comprising 2 wt. % phenol or less to a MEK recovery zone and exposing the CKC vapor condensate mixture to MEK recovery conditions effective to produce a MEK product.

98. The process of claim 96 further comprising feeding the CKC vapor condensate mixture to a MEK recovery zone and exposing the CKC vapor condensate mixture to MEK recovery conditions effective to produce a MEK product.

99. The process of claim 98 wherein the MEK recovery conditions comprise
mixing the CKC vapor condensation mixture with an amount of a MEK recovery alkali base effective to condense a majority of aldehydes in the CKC vapor condensate mixture with MEK and to convert a majority of phenol in the CKC vapor condensate mixture to sodium phenate, thereby producing a MEK recovery mixture; and,
subjecting the MEK recovery mixture to MEK separation conditions effective to separate a MEK product.

100. The process of claim 99 wherein the MEK recovery alkali base is sodium hydroxide.

101. The process of claim 99 wherein the MEK separation conditions comprise
cooling the MEK recovery mixture to a MEK recovery temperature of from about 35° C. to about 55° C. to produce a cooled MEK recovery mixture; and,
exposing the cooled MEK recovery mixture to MEK recovery mixture separation conditions effective to separate the cooled MEK recovery mixture into a first MEK aqueous stream and a first MEK organic stream.

102. The process of claim 101 wherein the MEK recovery temperature is from about 40° C. to about 45° C.

103. The process of claim 101 further comprising recirculating the first MEK aqueous stream to the cleavage neutralization apparatus.

104. The process of claim 101 further comprising
washing the first MEK organic stream with aqueous alkali base under first MEK organic stream washing conditions effective to remove trace phenol, producing a first washed MEK organic phase;
washing the first washed MEK organic phase with an aqueous wash under conditions effective to remove trace alkali base and to produce a twice washed MEK organic stream; and,
subjecting the twice washed MEK organic stream to twice washed MEK organic stream separation conditions effective to produce a twice washed MEK aqueous phase and a MDC feed comprising a twice washed MEK organic phase.

105. The process of claim 101 further comprising decanting the cooled MEK recovery mixture under MEK recovery mixture decanting conditions effective to separate the cooled MEK recovery mixture into a MEK decanter aqueous stream and a MEK decanter organic stream comprising MEK, hydrocarbon, other organic species, dissolved water, and combinations thereof.

106. The process of claim 105 further comprising recirculating the MEK decanter aqueous stream to the cleavage neutralization apparatus.

107. The process of claim 105 further comprising
subjecting the first washed MEK organic stream to first washed MEK organic stream separation conditions effective to produce a first washed MEK aqueous phase and a first washed MEK organic, producing a first washed MEK decanter organic stream;
washing the MEK decanter organic stream with aqueous alkali base under MEK-decanter organic stream washing conditions effective to remove trace phenol;
separating the first washed MEK decanter organic stream under first washed MEK decanter organic stream separating conditions effective to separate the first washed MEK decanter organic stream into a first washed MEK decanter aqueous phase and a first washed MEK decanter organic phase;
washing the first washed MEK decanter organic phase with an aqueous wash under conditions effective to remove trace alkali base and to produce a twice washed MEK decanter organic stream;
exposing the twice washed MEK decanter organic stream to twice washed MEK decanter organic stream separation conditions effective to produce a twice washed MEK decanter aqueous phase and an MDC feed comprising a twice washed MEK decanter organic phase, the MDC feed comprising MEK, hydrocarbon, water, other organic species, and combinations thereof.

108. The process of claim 107 further comprising subjecting said MDC feed to MDC conditions effective to produce a MDC overhead comprising water and organic species having a boiling point sufficiently lower than MEK to be separated from the MEK.

109. The process of claim 108 wherein the MDC conditions comprise a MDC entrainer effective to remove water from the MDC feed.

110. The process of claim 109 wherein the MDC entrainer is selected from the group consisting of hexane, cyclohexane, heptane, and combinations thereof.

111. The process of claim 109 wherein the MDC entrainer is cyclohexane.

112. The process of claim 108 wherein the MDC conditions comprise
a MDC pressure of from about 3 to about 10 psig;
a MDC temperature of from about 75° C. to about 90° C.; and,
a minimum MDC molar reflux ratio of about 5/1 based on the reflux flow to the overhead water flow.

113. The process of claim 108 wherein the MDC conditions comprise
a MDC pressure of from about 6 to about 7 psig;
a MDC temperature of from about 80° C. to about 85° C.; and,
a MDC molar reflux ratio of from about 10/1 to about 20/1 based on the reflux flow to the overhead water flow.

114. The process of claim 108 further comprising subjecting the MDC bottoms to MPC conditions effective to separate the MDC bottoms into a MPC bottoms comprising hydrocarbons and organic species having a boiling point higher than MEK and a MPC overhead comprising product MEK.

115. The process of claim 114 wherein the MPC overhead comprises a MPC purge stream comprising MEK, the MPC purge stream being effective to purge organic species having a boiling point less than MEK from the MPC.

116. The process of claim 114 wherein the MPC conditions are effective to produce MEK product as a side draw from the MPC.

117. The process of claim 115 wherein the MPC conditions are effective to produce MEK product as a side draw from the MPC.

118. The process of claim 114 wherein the MPC conditions comprise
a MPC top pressure of from about 0 psig to about 10 psig;
a MPC top temperature of from about 85° C. to about 101° C.; and,
a MPC molar reflux ratio, based on reflux flow to MEK product flow, of 0.15 or greater.

119. The process of claim 114 wherein the MPC conditions comprise
a MPC top pressure of from about 4 psig to about 6 psig;
a MPC top temperature of from about 92° C. to about 95° C.; and,
a MPC molar reflux ratio, based on reflux flow to MEK product flow, of greater than 0.15.

120. The process of claim 119 wherein the MPC molar reflux ratio is from about 0.15 to about 1.

121. The process of claim 119 wherein the MPC molar reflux ratio is about 1/1.

122. A process for producing controllable yields of a combination of products selected from the group consisting of (a) phenol and methyl ethyl ketone (MEK) and (b) phenol, acetone, and MEK, said process comprising:
feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene;
exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
cleaving the product hydroperoxides under cleavage conditions effective to produce a cleavage product comprising a combination selected from the group consisting of (a) phenol and MEK, and (b) phenol, acetone, and MEK; and,
separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
recovering one or more products selected from the group consisting of (a) an MEK product and (b) a combination comprising an MEK product and an acetone product,
wherein the acetone/MEK separation conditions comprise feeding the acetone/MEK stream to an Acetone Product Column (APC) as an APC feed and subjecting the APC feed to APC conditions effective to produce an APC product comprising an APC overhead comprising an APC purge stream comprising acetone, said APC product further comprising substantially pure product acetone as a side draw.

123. The process of claim 85 wherein the acetone/MEK separation conditions comprise feeding the acetone/MEK stream to an Acetone Product Column (APC) as an APC feed and subjecting the APC feed to APC conditions effective to produce an APC product comprising an APC overhead comprising an APC purge stream comprising acetone, said APC product further comprising substantially pure product acetone as a side draw.

124. The process of claim 123 wherein the CKC conditions are effective to produce an APC feed comprising less than 2 wt. % phenol.

125. The process of claim 124 wherein the CKC conditions are effective to produce an APC feed comprising from about 14 wt. % to about 45 wt. % acetone and from about 46 wt. % to about 15 wt. % MEK.

126. The process of claim 123 wherein the oxidation feed comprises from about 15 wt. % to about 30 wt. % cumene, and the CKC conditions are effective to produce an APC feed comprising from about 16 to about 28 wt. % acetone and from about 44 to about 32 wt. % MEK, respectively.

127. The process of claim 123 further comprising feeding to the first cleavage reactor an amount of a recycle stream effective to reduce the production of non-recoverable by-products from DMBA, EMBA, and a combination thereof, said recycle stream being selected from the group consisting of the MPC purge stream, the APC purge stream, and a combination thereof.

128. The process of claim 127 wherein said amount of said recycle stream is about 0.1 pound or more of recycle stream per pound of third stripper bottoms.

129. The process of claim 123 wherein the APC conditions comprise
feeding to the APC column an APC base effective to catalyze the condensation of aldehydes in the APC feed with MEK and acetone to produce an APC bottoms comprising MEK, hydrocarbon, APC condensation reaction products, sodium phenate, and combinations thereof; and, subjecting the APC bottoms to MEK separation conditions effective to separate MEK product.

130. The process of claim 129 wherein the APC base is an alkali base.

131. The process of claim 129 wherein the APC base is sodium hydroxide.

132. The process of claim 123 wherein the APC conditions comprise
an APC top pressure of from about 400 to about 500 mm Hg;
an APC top temperature of from about 30° C. to about 50° C.; and,
a minimum APC molar reflux ratio is about 12/1.

133. The process of claim 123 wherein the APC conditions comprise
an APC top pressure of about 450 mm Hg;
an APC top temperature of about 40° C.; and,
an APC molar reflux ratio of from about 15/1 to about 27/1, calculated as rate of reflux flow to side draw product flow on a molar basis.

134. The process of claim 133 wherein the APC molar reflux ratio is about 21/1 or greater, calculated as rate of reflux flow to side draw product flow on a molar basis.

135. The process of claim 129 wherein the MEK separation conditions comprise
cooling the APC bottoms to a cooled APC bottoms temperature of from about 35° C. to about 55° C.; and,
exposing the cooled APC bottoms to cooled APC bottoms separation conditions effective to produce an APC aqueous stream and an APC organic stream comprising MEK, hydrocarbon, other organic species, dissolved water, and combinations thereof.

136. The process of claim 135 wherein said cooled APC bottoms temperature is from about 40° C. to about 45° C.

137. The process of claim 135 further comprising recycling the APC aqueous stream to the cleavage neutralization apparatus.

138. The process of claim 135 further comprising
washing the APC organic stream with aqueous alkali base under APC organic stream washing conditions effective to remove trace phenol and to produce a first washed APC organic stream;
separating the first washed APC organic stream under first washed APC separation conditions effective to separate the first washed APC organic stream into a first washed APC aqueous phase and a first washed APC organic phase;
washing the first washed APC organic phase with an aqueous wash under conditions effective to remove trace alkali base and to produce a twice washed APC organic stream; and,
separating the twice washed APC organic stream under twice washed APC organic stream separation conditions effective to produce a twice washed APC aqueous phase and a MDC feed comprising a twice washed APC organic phase.

139. The process of claim 138 wherein the APC organic stream separation conditions are decanter separation conditions.

140. The process of claim 135 wherein the cooled APC bottoms separation conditions comprise decanting the cooled APC bottoms into an APC decanter aqueous stream and an APC decanter organic stream comprising MEK, hydrocarbon, other organic species, dissolved water, and combinations thereof.

141. The process of claim 138 wherein the cooled APC bottoms separation conditions comprise decanting the cooled APC bottoms into an APC decanter aqueous stream and an APC decanter organic stream comprising MEK, hydrocarbon, other organic species, dissolved water, and combinations thereof.

142. The process of claim 141 further comprising recycling the APC decanter aqueous stream to the cleavage neutralization apparatus.

143. The process of claim 141 further comprising
washing the APC decanter organic stream with aqueous alkali base under APC decanter organic stream washing conditions effective to remove trace phenol and to produce a first washed APC decanter organic stream;
separating the first washed APC decanter organic stream under first washed APC decanter organic stream separation conditions effective to produce a first washed APC decanter aqueous phase and a first washed APC decanter organic phase.

144. A process for producing controllable yields of a combination of products selected from the group consisting of (a) phenol and methyl ethyl ketone (MEK) and (b) phenol, acetone, and MEK, said process comprising:
feeding an oxidation feed to an oxidation reactor to produce an oxidation mixture, the oxidation feed comprising one or more alkylbenzenes selected from the group consisting of (a) a content of s-butylbenzene, and (b) a combination of s-butylbenzene and cumene at a weight ratio of cumene to s-butylbenzene;
exposing the oxidation mixture to oxidation conditions effective to produce an oxidation product stream comprising product hydroperoxides selected from the group consisting of (a) s-butylbenzene hydroperoxide, and (b) a combination of s-butylbenzene hydroperoxide and cumene hydroperoxide;
cleaving the product hydroperoxides under cleavage conditions effective to produce a cleavage product comprising a combination selected from the group consisting of (a) phenol and MEK, and (b) phenol, acetone, and MEK; and,
separating the cleavage product under separation conditions effective to separate a crude phenol fraction comprising phenol and a crude ketone stream selected from the group consisting of (a) a crude MEK stream and (b) a crude acetone/MEK stream comprising MEK and acetone; and,
recovering one or more products selected from the group consisting of (a) an MEK product and (b) a combination comprising an MEK product and an acetone product,
wherein said oxidation mixture further comprises an amount of oxidation base effective to increase production of said product hydroperoxide and decrease production of byproducts from components selected from the group consisting of AR DMBA, EMBA, and combinations thereof, said oxidation base comprising a quantity of water insufficient to create a separate aqueous phase.

145. The process of claim 144 wherein said oxidation base is selected from the group consisting of alkali bases, anhydrous ammonia, and aqueous ammonia.

146. The process of claim 144 wherein said alkali base is selected from the group consisting of alkali metal carbonates and alkali metal bicarbonates.

147. The process of claim 144 wherein said oxidation base is aqueous ammonia comprising an amount of water effective to increase neutralization of acids formed during the oxidation by the oxidation base.

148. The process of claim 144 wherein said amount of water is from about 400 ppm to about 2 wt. %.

149. The process of claim 144 wherein said amount of oxidation base is sufficient to produce a ratio of base to acids of from about 0:1 to about 6:1.

150. The process of claim 144 wherein said amount of oxidation base is sufficient to produce a ratio of base to acids of from about 0.5:1 to about 4:1.

151. The process of claim 147 wherein said amount of oxidation base is sufficient to produce a ratio of base to acids formed under said oxidation conditions of from about 0:1 to about 6:1.

152. The process of claim 148 wherein said amount of oxidation base is sufficient to produce a ratio of base to acids formed under said oxidation conditions of from about 0:1 to about 6:1.

153. The process of claim 148 wherein said amount of base is sufficient to produce a ratio of neutralizing base to acids formed under said oxidation conditions of from about 0.5:1 to about 4:1.

154. A process for producing controllable yields of a combination of products selected from the group consisting of (a) phenol and MEK, and (b) phenol, acetone, and MEK, said process comprising:

feeding an oxidation feed to a series of continuous oxidation reactors to produce an oxidation mixture and feeding a source of molecular oxygen to the oxidation mixture, the oxidation feed comprising one or more alkylbenzenes selected from the group consisting of (a) a content of s-butylbenzene (b) a combination comprising s-butylbenzene and cumene at a cumene:s-butylbenzene ratio;

exposing the oxidation mixture to oxidation conditions effective to produce an oxidation product stream comprising product hydroperoxides selected from the group consisting of (a) s-butylbenzene hydroperoxide, and (b) a combination comprising s-butylbenzene hydroperoxide and cumene hydroperoxide;

separating the oxidation product stream under oxidation separation conditions effective to produce an OB and an oxidation vapor overhead;

feeding the OB and a quantity of water to one or more strippers and exposing the OB to stripping conditions effective to concentrate but ineffective to decompose said product hydroperoxides, the stripping conditions being effective to produce a stripper overhead and a stripper bottoms comprising the hydroperoxides, said quantity of water being effective to produce a first condenser vapor phase comprising a majority of water, ethanol, methanol, methyl hydroperoxide, ethyl hydroperoxide, and combinations thereof, in the first stripper overhead;

wherein the stripping conditions comprise
first stripper conditions effective to produce a first stripper bottoms and a first stripper overhead comprising a portion of the one or more alkylbenzenes;
second stripper conditions effective to produce a second stripper overhead and a second stripper bottoms, and
third stripper conditions effective to produce a third stripper overhead and third stripper bottoms,
wherein said stripping conditions comprise a first stripper pressure greater than a second stripper pressure greater than a third stripper pressure;

exposing the first stripper overhead to first stripper overhead condenser conditions comprising a first stripper overhead condensation temperature and a first stripper overhead condensation pressure, said first stripper overhead condenser conditions being effective to cause a majority of the one or more alkylbenzenes in the first stripper overhead to condense, producing a first condenser organic phase, said first stripper overhead condenser conditions and said quantity of water also being effective to produce a first condenser vapor phase comprising a majority of water, ethanol, methanol, methyl hydroperoxide, ethyl hydroperoxide, and combinations thereof, in the first stripper overhead;

separating the first condenser vapor phase from the first condenser organic phase;

subjecting the first condenser vapor phase to second condensation conditions effective to form a second condenser organic phase and a second condenser aqueous phase comprising a majority of each of the ethanol, the methanol, the methyl hydroperoxide, the ethyl hydroperoxide, and combinations thereof in the first condenser vapor phase;

decomposing the second condenser aqueous phase under thermal decomposition conditions effective to decompose hydroperoxides selected from the group consisting of ethyl hydroperoxide, methyl hydroperoxide, and combinations thereof, to produce a thermal decomposition product comprising alcohols, aldehydes, carboxylic acids, and combinations thereof, said thermal decomposition conditions comprising a thermal decomposition temperature of from about 80° C. to 250° C. and a thermal decomposition pressure of from about 100 psig to about 200 psig;

feeding to a first cleavage reactor at least a portion of the third stripper bottoms and an acid catalyst to produce a first cleavage reaction mixture, said acid catalyst being effective to catalyze the cleavage of hydroperoxides selected from the group consisting of s-butylbenzene hydroperoxide, cumene hydroperoxide, and combinations thereof, exposing the first cleavage reaction mixture to first cleavage reaction conditions effective to produce a first cleavage reaction product, said first cleavage reaction conditions comprising a first cleavage reaction temperature of from about 45° C. to about 70° C., a first cleavage reaction pressure sufficiently high to maintain the first cleavage reaction mixture in the liquid phase, and a first cleavage reaction residence time of from about 1 to about 10 minutes;

subjecting the first cleavage reaction product to second cleavage reaction conditions effective to produce a second cleavage reaction product, said second cleavage reaction conditions comprising a second cleavage reaction temperature of from about 60° C. to about 130° C., a second cleavage reaction pressure sufficient to maintain the second cleavage reaction mixture in the liquid phase, and a first cleavage reaction residence time of from about 5 seconds to about 1 minute;

cooling and neutralizing the second cleavage reaction product with a second cleavage reaction product neutralizing base under second cleavage reaction product neutralization conditions effective to produce a neutralized second cleavage reaction product, said second cleavage reaction product neutralization conditions comprising a second cleavage reaction product neutralization pressure sufficient to maintain the second cleavage reaction product in the liquid phase; and, separating the neutralized second cleavage reaction product into a neutralized second cleavage reaction product aqueous fraction and a CKC feed comprising a neutralized second cleavage reaction product organic fraction;

feeding the CKC feed to a Crude Ketone Column (CKC) and exposing the CKC feed to CKC conditions effective to produce a crude phenol fraction comprising from about 2 wt. % to about 5 wt. % of the one or more alkylbenzenes, AMS, AES, 2P2B, and a CKC vapor distillate comprising most of the one or more alkylbenzenes, water, AMS, AES, 2P2B, and combinations thereof in the CKC feed;

condensing the CKC vapor distillate to produce a CKC vapor condensate, said condensing comprising feeding the CKC vapor distillate to a CKC vapor condenser and subjecting the CKC vapor distillate to CKC vapor condenser conditions effective to produce the CKC vapor condensate; and, exposing the CKC vapor condensate to CKC vapor condensate separation conditions effective to produce a CKC vapor condensate organic layer and a CKC vapor condensate aqueous layer;

feeding a CKC recycle portion of the CKC vapor condensate aqueous layer to the CKC column at a recycle point;

mixing a remainder of the CKC vapor condensate aqueous layer with the CKC vapor condensate organic layer to form a CKC vapor condensate mixture comprising 2 wt. % phenol or less;

recovering a product selected from the group consisting of (a) a MEK product and (b) a combination comprising a MEK product and an acetone product.

155. The process of claim 154 said recovering a product comprises recovering a MEK product, said process further comprising:

mixing the CKC vapor condensate mixture with an amount of a MEK recovery alkali base effective to condense a majority of aldehydes in the CKC vapor condensate mixture with MEK and to convert a majority of phenol in the CKC vapor condensate to sodium phenate, thereby producing a MEK recovery mixture; and, cooling the MEK recovery mixture to a MEK recovery temperature of from about 35° C. to about 55° C. to produce a cooled MEK recovery mixture;

decanting the cooled MEK recovery mixture under MEK recovery mixture decanting conditions effective to separate the cooled MEK recovery mixture into a MEK decanter aqueous stream and a MEK decanter organic stream comprising MEK, hydrocarbon, other organic species, dissolved water, and combinations thereof;

washing the MEK decanter organic stream with aqueous alkali base under MEK decanter organic stream washing conditions effective to remove trace phenol, producing a first washed MEK decanter organic stream;

separating the first washed MEK decanter organic stream under first washed MEK decanter organic stream separating conditions effective to separate the first washed MEK decanter organic stream into a first washed MEK decanter aqueous phase and a first washed MEK decanter organic stream;

washing the first washed MEK decanter organic stream with an aqueous wash under conditions effective to remove trace alkali base and to produce a twice washed MEK decanter organic stream;

exposing the twice washed MEK decanter organic stream to twice washed MEK decanter organic phase separation conditions effective to produce a twice washed MEK decanter aqueous phase and a MDC feed comprising a twice washed MEK decanter organic phase comprising MEK, hydrocarbon, water, other organic species, and combinations thereof;

subjecting the MDC feed to MDC conditions effective to produce a MDC overhead comprising water and organic species having a boiling point sufficiently lower than MEK to be separated from the MEK, and a MDC bottoms comprising MEK hydrocarbon, and organic species having a boiling point the same as or greater than MEK;

subjecting the MDC bottoms to MPC conditions effective to separate the MDC bottoms into a MPC bottoms comprising hydrocarbons and organic species having a boiling point higher than MEK and a MPC overhead comprising an MPC purge stream comprising MEK, said MPC conditions also being effective to produce MEK product as a side draw from the MPC.

156. The process of claim 154 wherein said recovering a product comprises recovering a MEK product and an acetone product, said process further comprising:

feeding the CKC vapor condensate mixture to an Acetone Product Column (APC) as an APC feed and subjecting the APC feed to APC conditions effective to produce an APC product comprising an APC overhead comprising an APC purge stream comprising acetone, said APC product further comprising substantially pure product acetone as a side draw;

wherein the APC conditions comprise:

feeding to the APC column an APC base effective to catalyze the condensation of aldehydes in the APC feed with MEK and acetone to produce an APC bottoms comprising MEK, hydrocarbon, APC condensation reaction products, sodium phenate, and combinations thereof; and, subjecting the APC bottoms to MEK separation conditions effective to separate MEK product.

157. The process of claim 156 wherein the MEK separation conditions comprise:

cooling the APC bottoms to a temperature of from about 35° C. to about 55° C.;

exposing the cooled APC bottoms to APC separation conditions effective to produce a first APC aqueous stream and a first APC organic stream comprising MEK, hydrocarbon, other organic species, dissolved water, and combinations thereof;

washing the first APC organic stream with aqueous alkali base under first APC organic stream washing conditions effective to remove trace phenol and to produce a first washed APC organic stream;

exposing the first washed APC organic stream to first washed APC organic stream separation conditions effective to produce a first washed APC aqueous phase and a first washed APC organic phase;

washing the first washed APC organic phase with an aqueous wash under conditions effective to remove trace alkali base and to produce a twice washed APC organic stream; and, separating the twice washed APC organic stream under twice washed APC organic stream separation conditions effective to produce a MDC feed comprising a twice washed APC organic phase and a twice washed APC aqueous phase.

158. The process of claim 156 wherein the MEK separation conditions comprise:

cooling the APC bottoms to a temperature of from about 35° C. to about 55° C.;

decanting the cooled APC bottoms into a cooled APC decanter aqueous stream and a cooled APC decanter organic stream comprising MEK, hydrocarbon, other organic species, dissolved water, and combinations thereof;

washing the cooled APC decanter organic stream with aqueous alkali base under APC decanter organic stream washing conditions effective to remove trace phenol and to produce a first washed APC decanter organic stream; and, exposing the first washed APC decanter organic stream to APC decanter organic stream separation conditions effective to produce a first washed APC decanter aqueous phase and a first washed APC decanter organic phase.

159. The process of claim 154 further comprising feeding to a first cleavage reactor an amount of a recycle stream effective to reduce the production of non-recoverable by-products from DMBA, EMBA, and a combination thereof, said recycle stream being selected from the group consisting of the MPC purge stream, the APC purge stream, and a combination thereof.

160. The process of claim 155 further comprising feeding to the first cleavage reactor an amount of a recycle stream effective to reduce the production of non-recoverable by-products from DMBA, EMBA, and a combination thereof, said recycle stream being selected from the group consisting of the MPC purge stream, the APC purge stream, and a combination thereof.

161. The process of claim 156 further comprising feeding to the first cleavage reactor an amount of a recycle stream effective to reduce the production of non-recoverable by-products from DMBA, EMBA, and a combination thereof, said recycle stream being selected from the group consisting of the MPC purge stream, the APC purge stream, and a combination thereof.

162. The process of claim 157 further comprising feeding to the first cleavage reactor an amount of a recycle stream effective to reduce the production of non-recoverable by-products from DMBA, EMBA, and a combination thereof, said recycle stream being selected from the group consisting of the MPC purge stream, the APC purge stream, and a combination thereof.

163. The process of claim 158 further comprising feeding to the first cleavage reactor an amount of a recycle stream effective to reduce the production of non-recoverable by-products from DMBA, EMBA, and a combination thereof, said recycle stream being selected from the group consisting of the MPC purge stream, the APC purge stream, and a combination thereof.

164. The process of claim 154 wherein the MDC conditions comprise a MDC entrainer effective to remove water from the MDC feed.

165. The process of claim 164 wherein the MDC entrainer is selected from the group consisting of hexane, cyclohexane, heptane, and combinations thereof.

166. The process of claim 164 wherein the MDC entrainer is cyclohexane.

167. The process of claim 163 wherein the MDC conditions comprise a MDC entrainer effective to remove water from the MDC feed.

168. The process of claim 167 wherein the MDC entrainer is selected from the group consisting of hexane, cyclohexane, heptane, and combinations thereof.

169. The process of claim 167 wherein the MDC entrainer is cyclohexane.

170. The process of claim 154 wherein said oxidation mixture further comprises an amount of oxidation base effective to increase production of said product hydroperoxide and decrease production of byproducts from components selected from the group consisting of AP, DMBA, EMBA, and combinations thereof, said oxidation base comprising a quantity of water insufficient to create a separate aqueous phase.

171. The process of claim 170 wherein said oxidation base is selected from the group consisting of alkali bases, anhydrous ammonia, and aqueous ammonia.

172. The process of claim 171 wherein said alkali base is selected from the group consisting of alkali metal carbonates and alkali metal bicarbonate.

173. The process of claim 170 wherein said oxidation base is aqueous ammonia comprising an amount of water effective to increase neutralization of acids formed during the oxidation by the oxidation base.

174. The process of claim 170 wherein said amount of water is from about 400 ppm to about 2 wt. %.

175. The process of claim 170 wherein said amount of oxidation base is sufficient to produce a ratio of base to acids of from about 0:1 to about 6:1.

176. The process of claim 170 wherein said amount of oxidation base is sufficient to produce a ratio of base to acids of from about 0.5:1 to about 4:1.

177. The process of claim 173 wherein said amount of oxidation base is sufficient to produce a ratio of base to acids formed under said oxidation conditions of from about 0:1 to about 6:1.

178. The process of claim 174 wherein said amount of oxidation base is sufficient to produce a ratio of base to acids formed under said oxidation conditions of from about 0:1 to about 6:1.

179. The process of claim 174 wherein said amount of oxidation base is sufficient to produce a ratio of base to acids formed under said oxidation conditions of from about 0.5:1 to about 4:1.

180. The process of claim 169 wherein said oxidation mixture further comprises an amount of oxidation base effective to increase production of said product hydroperoxide and decrease production of byproducts from components selected from the group consisting of AP, DMBA, EMBA, and combinations thereof, said neutralizing base comprising a quantity of water insufficient to create a separate aqueous phase.

181. The process of claim 180 wherein said oxidation base is selected from the group consisting of alkali bases, anhydrous ammonia, and aqueous ammonia.

182. The process of claim 181 wherein said alkali base is selected from the group consisting of alkali metal carbonates and alkali metal bicarbonate.

183. The process of claim 181 wherein said oxidation base is aqueous ammonia comprising an amount of water effective to increase neutralization of acids formed during the oxidation by the oxidation base.

184. The process of claim 180 wherein said amount of water is from about 400 ppm to about 2 wt. %.

185. The process of claim 180 wherein said amount of oxidation base is sufficient to produce a ratio of base to acids of from about 0:1 to about 6:1.

186. The process of claim 180 wherein said amount of oxidation base is sufficient to produce a ratio of base to acids of from about 0.5:1 to about 4:1.

187. The process of claim 184 wherein said amount of oxidation base is sufficient to produce a ratio of base to acids formed under said oxidation conditions of from about 0:1 to about 6:1.

188. The process of claim 185 wherein said amount of oxidation base is sufficient to produce a ratio of base to acids formed under said oxidation conditions of from about 0:1 to about 6:1.

189. The process of claim 185 wherein said amount of oxidation base is sufficient to produce a ratio of base to acids formed under said oxidation conditions of from about 0.5:1 to about 4:1.

190. The process of claim 154 wherein said oxidation separation conditions comprise washing said oxidation product stream under oxidation product washing conditions effective to remove salts formed in the oxidation and to produce said first condenser vapor phase.

191. The process of claim 189 wherein said oxidation separation conditions comprise washing said oxidation product stream under oxidation product washing conditions effective to remove salts formed in the oxidation and to produce said first condenser vapor phase.

* * * * *